(12) United States Patent
Berg

(10) Patent No.: US 7,585,890 B2
(45) Date of Patent: Sep. 8, 2009

(54) PHARMACEUTICAL COMPOSITIONS COMPRISING FLAVONOIDS AND MENTHOL

(75) Inventor: Kurt Frimann Berg, Charlottenlund (DK)

(73) Assignee: Immunpharm A/S, Alborg O (DK)

( * ) Notice: Subject to any disclaimer, the term of this patent is extended or adjusted under 35 U.S.C. 154(b) by 246 days.

(21) Appl. No.: 10/532,341

(22) PCT Filed: Sep. 19, 2003

(86) PCT No.: PCT/DK03/00608

§ 371 (c)(1),
(2), (4) Date: Apr. 22, 2005

(87) PCT Pub. No.: WO2004/037237

PCT Pub. Date: May 6, 2004

(65) Prior Publication Data

US 2006/0148726 A1   Jul. 6, 2006

(30) Foreign Application Priority Data

Oct. 24, 2002   (DK) ................................ 2002 01614

(51) Int. Cl.
*A61K 31/353* (2006.01)
(52) U.S. Cl. ...................................... 514/456
(58) Field of Classification Search ................. 514/456
See application file for complete search history.

(56) References Cited

U.S. PATENT DOCUMENTS

| | | | |
|---|---|---|---|
| 5,846,557 A | 12/1998 | Eisenstadt et al. |
| 6,063,383 A | 5/2000 | Hsu et al. |
| 6,224,872 B1 | 5/2001 | Shibuya et al. |
| 6,294,186 B1 | 9/2001 | Beerse et al. |
| 6,410,062 B1 | 6/2002 | Callaghan et al. |
| 6,579,543 B1 | 6/2003 | McClung |
| 6,592,896 B2 | 7/2003 | Rosenbloom |
| 6,596,313 B2 | 7/2003 | Rosenbloom |

FOREIGN PATENT DOCUMENTS

| | | |
|---|---|---|
| CN | 1280836 | 7/2000 |
| EP | 0288077 | 10/1988 |
| EP | 0711560 | 5/1996 |
| EP | 0809488 | 8/1996 |
| EP | 1072254 | 1/2001 |
| EP | 0867187 | 7/2003 |
| JP | 2059513 | 2/1990 |
| JP | 291441 | 10/2002 |
| JP | 363006 | 12/2002 |
| WO | 8500112 | 1/1985 |
| WO | 0037044 | 6/2000 |
| WO | 0103681 | 1/2001 |
| WO | 0149285 | 7/2001 |
| WO | 0195900 | 12/2001 |
| WO | 0205802 | 1/2002 |
| WO | WO 02/05802 | 1/2002 |
| WO | 0209699 | 2/2002 |
| WO | 03013428 | 2/2003 |

OTHER PUBLICATIONS

Eccles, R., et al, "Menthol and Related Cooling Compounds" 1994, J.Pharm. Pharmacol., 46, (Review): 618-630.
Eccles, R., et al, "The effects of oral administration of (—)-methol on nasal resistance to airflow and nasal sensation of airflow in subjects suffering from nasal congestion associated with the common cold" 1990, J. Pharm Pharmacol., 42, (9): 652-654.
Eccles, R., et al, "The effects of methol on reaction time and nasal sensation of airflow in subjects suffering from the common cold" 1990, Clin. Otolaryngol, 15: 39-42.
Duband et al., "Composition aromatique et polyphenolique de l'infuse de Menth, Mentha X piperita L" 1992, Annales Pharmaceutique Francises, 50: 146-55, Abstract Only.
Ahlgrimm, 1956, "Beitrage zur frage der biogenese sekundarer stoffwechselprodukte dargestellt an mentha piperita I und an fagopyrumarten" Planta, 47:255-98, Abstract Only.

*Primary Examiner*—Taofiq A Solola
(74) *Attorney, Agent, or Firm*—Iver P. Cooper

(57) ABSTRACT

The present invention relates to use of certain antiviral fragrances for reduction of viruses, in particular vira causing common cold. In one embodiment, the invention relates to pharmaceutical compositions comprising an antiviral fragrance, preferably menthol. Said compositions preferably also comprise one or more flavonoids. The invention also relates to treatment of common cold using said compositions.

30 Claims, 13 Drawing Sheets

PHARMACEUTICAL COMPOSITIONS COMPRISING FLAVONOIDS AND MENTHOL

FIELD OF THE INVENTION

The present invention relates to the field of pharmaceutical compositions comprising flavonoids. In particular, the invention relates to pharmaceutical compositions comprising flavonoids and menthol. The invention furthermore relates to methods of treatment using said compositions, for example to methods of treating common cold or similar conditions.

BACKGROUND OF THE INVENTION

Common cold is in general initiated by viral infections by the so-called cold viruses, such as rhino virus, corona virus, adenovirus, coxsackie virus, RS-virus, echovirus or other cold viruses. In average all human beings suffer 2 to 3 times a year from infections in the upper respiratory passages, such as cold and flu. In general, in Denmark the majority of common colds occurring in September, October and November are caused by rhinovirus infection, whereas the majority of common cold occurring in January, February and March are caused by Coronavirus infections. In addition, allergic syndromes, for example asthma, may be initiated by common cold viruses, especially the rhinovirus.

Recent observations from a polymerase chain reaction (PCR)-study (Johnston, 1993) with naturally rhinovirus infected persons indicates that the actual range for rhinovirus infections involved in common cold syndrome probably is at least twofold higher, compared to findings obtained via the traditional cell culture techniques (40%). This indicates that up to 70-75% of all patients suffering from common colds have a rhinovirus infections ongoing either as a single infection or co-infection (Spector, 1995).

It has been estimated that the average pre-school child experiences 6-10 upper respiratory infections or common colds per year whereas the average adult experiences 2-4 (Sperber, 1989). The effects of the common cold can be uncommonly disruptive, forcing otherwise normal persons to stay away from work, school, etc. Individuals who are at increased risks, such as individuals suffering from bronchitis or asthma, may also experience a life-threatening exacerbation of their underlying conditions. The average annual expenditure for various cold treatments exceeds USD 2 billion in the United States, alone (Spector, 1995); in the EU a similar figure is expected.

Unfortunately, research in development of novel strategies to treat common cold is complicated by the fact human rhinoviruses only have been reported to infect primates successfully and hence no practical animal model has been developed for rhinovirus infections (Rotbart, 2000).

The development of natural and experimentally induced rhinovirus infections in normal persons are initiated by selected events, which can be considered to occur sequentially. The steps in the rhinovirus pathogenesis are believed to include viral entry into the outer nose, mucociliary transport of virus to the posterior pharynx, and initiation of infection in ciliated and non-ciliated epithelial cells of the upper airway. Viral replication peaks on average within 48 h of initiation of infection and persists for up to 3 weeks; Infection is followed by activation of several inflammatory mechanisms, which may include release or induction of interleukins, bradykinins, prostaglandins and possibly histamine, including stimulation of parasympathetic reflexes (the cytokines may counteract each other at certain levels resulting in a very complex pathway). The resultant clinical illness is a rhinosinusitis, pharyngitis, and bronchitis, which on average lasts one week (Gwaltney, 1995).

Occasionally, a secondary bacterial or microbial infection may follow subsequently to the viral infection and a sustained and more serious inflammation may result.

Previously, it was believed that the major part of the virus was produced in the upper nose region and excreted (Winther, 1993a). However, subsequent studies, comparing recovery of virus in nasopharyngeal wash specimens, nasal swabs and pharyngeal swabs showed that the nasopharyngeal wash specimens was consistently superior to the other two specimens in yielding virus (Cate, 1964). From a series of in-depth investigations (Winther, 1984a; Winther, 1984b; Winther, 1984c; Turner, 1984; Farr, 1984; Hayden, 1987; Winther, 1987a; Winther, 1987b; Winther, 1993b; Arruda, 1995; Winther, 1998) it was concluded that:

(i) the virus was first recovered, at the highest concentrations, from the nasopharynx before it could be recovered in the upper nose region (turbinates).

(ii) no evidence for rhinovirus induced damage of the surface ciliary lining of the inferior turbinate was noted which is in agreement with other investigators suggesting that the virus may be transported to the nasopharynx in the overlaying mucus by mucociliary clearence.

(iii) there was a significant increase of the influx of neutrophils in the same area as in (ii)

(iv) infection of the lining of the nasal cavity was not uniform after intranasal inoculation and seemed not to result in any cell damage at all, cf. (ii) above.

(v) the rate of viral shedding in the nasopharynx was high by day 1 (post infection), whereas cold symptoms did not peak until day 3. The symptoms waned during the first week, but rhinovirus was present during the following 3 weeks.

(vi) The increase of neutrophils correlates with the onset of symptoms, including sore throat. The symptoms include oedema-like symptoms, which in turn may trigger sneezing and coughing.

It should be stressed that the highest concentration of virus can be recovered from the nasopharynx, and virus usually appears on the turbinate(s) one or two days later, despite the fact that virus is innoculated via the nose (in volunteers). No visible damage of the cell lining in the upper airways was ever demonstrated. Furthermore, as "sore throat" usually develops simultaneously with the appearance of virus in the nasopharynx it can be reasoned that "signal molecules" or the like (Van Damme, 1988) will be made by the relatively few rhinovirus cells infected and that these "cytokinelike molecules" subsequently may activate the "lymphatic ring"—which is located just beneath the nasopharynx—leading to the well-known sore throat, which in turn triggers a complex pattern of inflammatory reactions, involving an array of different interferons and cytokines the interaction of which is currently under in-depth investigation. Some of these factors, such as for example II-1, induce fever in patents. Bradykinines per se may be responsible for the sore throat, which is frequently associated with common cold.

The fact that interferon is known to be part of the non-specific innate immune response against viral infections in man has lead to several publications as a number of groups have investigated how much interferon is produced locally during viral infections of the upper-airways. One of the earliest and probably most thorough, in vivo, investigations in man was performed by Cate et al. (Cate, 1969) on volunteers (healthy adult males from federal correctional institutions in USA). The authors were able to demonstrate, that most of the persons involved produced interferon (as demonstrated in nasal washings) during common colds at a level, which at least theoretically should have been enough to block the viral infection, per se.

It has been demonstrated in a recent publication, that the immune system also takes "active part" in the spread of the inflammatory actions since experimental evidence supports the notion that rhinovirus may use some of the effector cells from the immune system as a mean for spreading the inflammatory reactions to the lower airways,(Gern, 1996) via initiation of local TNF-alpha production. It is tempting to speculate that the allergic rhinitis is initiated via this mechanism as it has been found that the pathogenesis for asthma is linked to local TNF-alpha production (Broide et al.1992). Several quarters have thus argued that the asthma syndromes are rhinovirus manifestations of post-infectious events triggered by an array of different cytokines in connection with a "switch" between the Th1 vs. Th2 response (Gern, 1999; Winther, 1998; Grünberg, 1999).

Generally speaking, air-way infections or allergic rhinitis and/or asthma may pose a serious health problems as it can be potentially life-threatening for susceptible groups such as elderly people with chronic airway problems or persons suffering from a deficient immunity, such as AIDS-patients, cancer patients etc. Thus, simple and effective methods of treating these symptoms/syndromes and possibly also the underlying infections would be of immense importance.

Viral and/or other microbial infections are known to initiate a complex inflammatory response (Ginsburg, 1988) from the patient which probably is mediated by several groups of responder cells including the neutrophile granulocytes, which are specifically increased during a cold. The latter represents approximately more than 95% of all the effector cells. Each min. about 6-9 millions neutrophiles enter the upper-airways and slowly pass down the interior surfaces encompassing the upper airways. It may be assumed that the neutrophiles, which are able to release very aggressive enzymes and toxic substances upon proper stimulation will keep the bacterial load of the upper-airways to an acceptable level. The small numbers of S. pyogenes or S. aureus found in nasopharynx, which otherwise is almost sterile, may stimulate the neutrophiles via the so-called super-antigens to a certain degree thereby limiting the numbers of bacteria in said areas (dynamic equilibrium/symbiosis).

According to Ihrcke and co-workers (Ihrcke, 1993) the very early steps in a virus infection (or any other abnormality in the cell lining) can be related to the content and metabolism of heparan sulfate proteoglycan (the major proteoglycan associated with intact endothelial cells). The first element of the model derives from the observation that heparan sulfate is released from the intact endothelial lining of blood vessels during the very first step in an inflammatory response initiated by a viral infection. Accordingly, this loss may seriously compromise the vascular integrity and result in a local edema attracting further neutrophiles via the up-regulation of ICAM-1 markers on the endothelial cells increasing the inflammatory response further. Thus, in a separate experiment, activated neutrophiles were able to release 70% of all cell-associated heparan sulfate proteoglycan within one hour via the subsequent release of heparanase. One important function of heparan sulfate is the maintenance of the endothelial cell integrity. Loss of heparan sulfate partially abrogates the barrier properties of the endothelium and contributes to the edema and exudation of plasma proteins that characterise inflammation.

It has previously been attempted to treat common cold using flavonoids.

WO 02/09699 describes treatment of common cold and similar conditions, such as hayfever using flavonoids, such as troxerutin or veneruton, either alone or in combination with metals. Flagrant used include peppermint oil.

U.S. Pat. No. 6,596,313 describes compositions for oral administration that may be useful for treatment of common cold. The compositions comprise extracts from various plants. The document mentions that menthol may be used as a flagrant. The effect of a composition comprising menthol is however not disclosed.

U.S. Pat. No. 6,592,896 describes oral pharmaceutical compositions comprising plant extracts. The document mentions that menthol may be used as a flagrant. The compositions may be useful for treatment of common cold. The effect of a composition comprising menthol is not disclosed.

WO 01/03681 describes treatment of viral infection, including infections related to common cold with a variety of flavonoids.

WO 01/49285 describes a medicament comprising flavonoid(s). The medicament may be useful for treatment of common cold, however this is not demonstrated.

SUMMARY OF THE INVENTION

It is an objective of the present invention to provide new and efficient pharmaceutical compositions for treatment of common cold and similar conditions. Interestingly, the present invention surprisingly discloses that the choice of fragrance is very important.

In particular, the present invention demonstrates a surprising effect amongst different commonly used fragrance additives. Interestingly, pharmaceutical compositions comprising flavonoid and purified menthol are more efficient than similar compositions comprising other fragrances in the treatment of common cold and related conditions.

Hence, it is a first objective of the present invention to provide pharmaceutical compositions comprising
  i) one or more purified flavonoids; and
  ii) purified menthol; and
  iii) pharmaceutically acceptable excipients.

It is a second objective of the present invention to provide use of one or more purified flavonoids and purified menthol for the preparation of a pharmaceutical composition for the treatment of a clinical condition or symptoms of a clinical condition in an individual in need thereof.

It is a third objective of the present invention to provide methods of treatment of a clinical condition in an individual in need thereof, comprising administering to said individual the pharmaceutical composition according to the invention.

It is a further objective of the present invention to provide a medicament for treating a clinical condition comprising purified flavonoid and purified menthol as active ingredients.

DETAILED DESCRIPTION

Pharmaceutical Compositions Comprising Flavonoid and Menthol

Figure 1A:
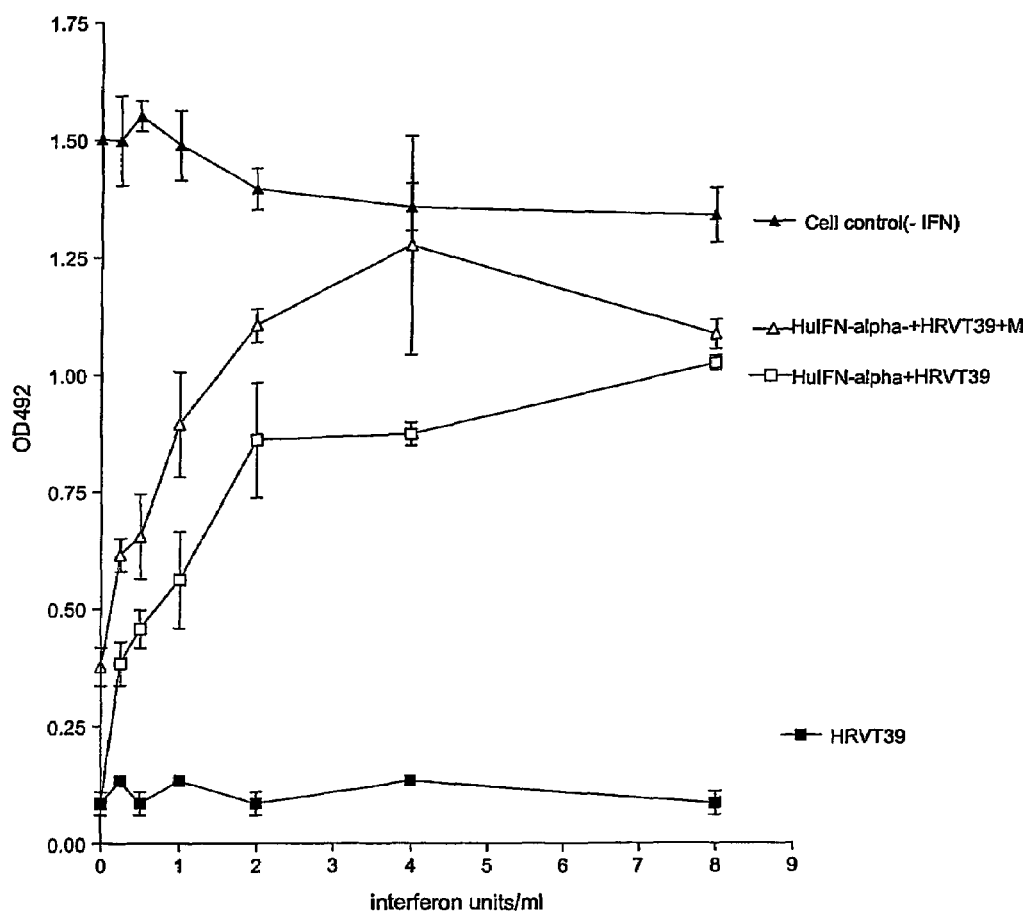
FIG. 1A illustrates the antiviral activity of natural HuIFN-α (designated HuIFN-alpha) versus rhinovirus-T39 at a dilution of $10^{-2}$ (designated HRV T39) in the presence and absence of menthol (1:800) (designated M).

Surprisingly, the present invention demonstrates that some fragrances, for example menthol has an antiviral effect, for example an antiviral effect against rhinovirus. Accordingly, in one embodiment the present invention relates to pharmaceutical compositions comprising flavonoid(s) and menthol as well as uses thereof.

In particular the pharmaceutical compositions preferably comprises
i) one or more purified flavonoids; and
ii) purified fragrance with antiviral effect; and
iii) pharmaceutically acceptable excipients.

Preferably, said fragrance with antiviral effect is menthol. However any other fragrances with antiviral effect, for example citric acid or similar compounds with low pH may be used.

In another embodiment the present invention relates to pharmaceutical compositions comprising one or more flavonoids, wherein said compositions are essentially free of any component of peppermint oil, which is not menthol. Preferably, said compositions are free of any components of Japanese peppermint oil. Said compositions may in addition to flavonoids comprise one or more other active ingredients, for example a metal salt and/or metal complex and/or menthol. The compositions may also comprise flavouring agents other than peppermint oil.

Components of peppermint oil may for example be selected from the group consisting of menthone, menthyl acetate, limonene, neomenthol, piperitone, menthenone, isomenthone, pulegone, β-caryophyllene, β-caryophyllene-epoxide, α-pinene,β-pinene, germacrene D, 1,8-cineol, linalool, menthofurane, camphene and β-hexenyl phenylacetate.

The flavonoid may be any of the flavonoids described herein below. Menthol is a terpene compound of the formula $CH_3C_6H_9(C_3H_7)OH$. Purified menthol may have been purified from a plant or it may have been synthesised chemically. Menthol purified from a plant is preferably essentially free of any other compounds of said plant. Menthol according to the invention is preferably levo-(–)-Menthol (also designated (–)-menthol). Useful pharmaceutical acceptable excipients are described herein below.

By the term "purified flavonoids" is meant one or more flavonoids essentially free of any other compounds. Hence, a composition of "purified flavonoids" comprises at least 90% flavonoid, preferably at least 95% flavonoid, more preferably at least 98% flavonoid, even more preferably approximately 100% flavonoid. A composition of "purified flavonoids" thus most preferably does not contain any other detectable compound. In particular, it is preferred that purified flavonoids are free of other compounds present in the composition from which they are purified. By way of example, if the flavonoid is purified from a plant extract, it is preferred that the purified flavonoids are essentially free of any other compounds present in the crude plant extract.

Preferably, the pharmaceutical compositions of the invention are essentially free of crude plant extracts or fractions thereof. The compositions may off course comprise fractions mainly consisting of flavonoids or menthol.

In one embodiment of the invention, purified flavonoids and purified menthol together constitutes at least 50%, preferably at least 60%, more preferably at least 70%, even more preferably at least 80%, yet more preferably at least 90%, even more preferably at least 95%, such as at least 98%, for example around 100% of the active ingredients of the pharmaceutical compositions of the invention.

Hence, in one preferred embodiment of the invention the pharmaceutical compositions essentially consists of
iv) one or more purified flavonoids; and
v) purified menthol; and
vi) pharmaceutically acceptable excipients, wherein said excipients are not therapeutically active.

By the term "essentially consists of" is meant that no other ingredients are detectable by commonly used detection techniques.

In another embodiment of the invention, the pharmaceutical compositions also comprise a pharmaceutically acceptable metal complex and/or metal salt. Examples of suitable metalcomplexes and salt are given herein below.

In this embodiment of the invention it is preferred, albeit not mandatory for the invention that purified flavonoids and purified menthol and metal complexes/metal salts together constitutes at least 50%, preferably at least 60%, more preferably at least 70%, even more preferably at least 80%, yet more preferably at least 90%, even more preferably at least 95%, such as at least 98%, for example around 100% of the active ingredients of the pharmaceutical compositions of the invention.

Hence, in a very preferred embodiment of the invention the pharmaceutical composition essentially consists of i) one or more purified flavonoids; and
ii) purified menthol; and
iii) one or more metal complexes and/or metal salts; and
iv) pharmaceutically acceptable excipients, wherein said excipients are not therapeutically active.

In one embodiment of the present invention it is thus preferred that the pharmaceutical compositions do not contain other active ingredients that the above mentioned, in particular it is preferred that the composition does not comprise any vitamins, such as vitamin E. It is also preferred that the composition does not comprise antibodies. It is also preferred that the compositions do not comprise hydroxypropylcellulose.

In one embodiment it is preferred that the pharmaceutical composition is essentially free of other terpenes than menthol. Hence, the pharmaceutical composition is in this embodiment of the invention preferably essentially free of one or more selected from the group consisting of menthone, menthyl acetate, limonene and neomenthol. More preferably, the composition is essentially free of one or more selected from the group consisting of menthone, menthyl acetate, limonene, neomenthol, piperitone, pulegone, β-caryophyllene, β-caryophyllene-epoxide, α-pinene, β-pinene, germacrene D, 1,8-cineol, linalool, menthofurane, camphene and β-hexenyl phenylacetate. Even more preferably, the pharmaceutical composition is essentially free of menthone, menthyl acetate, limonene and neomenthol. Yet more preferably, the pharmaceutical composition is essentially free of menthone, menthyl acetate, limonene, neomenthol, piperitone, pulegone, β-caryophyllene, β-caryophyllene-epoxide, α-pinene, β-pinene, germacrene D, 1,8-cineol, linalool, menthofurane, camphene and β-hexenyl phenylacetate. It is also preferred that the pharmaceutical composition is essentially free of one or more preferably all compounds selected from the group consisting of menthone, menthyl acetate, limonene, neomenthol, piperitone, menthenone, isomenthone, pulegone, β-caryophyllene, β-caryophyllene-epoxide, α-pinene, β-pinene, germacrene D, 1,8cineol, linalool, menthofurane, camphene and β-hexenyl phenylacetate.

The term "pharmaceutical composition" should be understood in its ordinary meaning, i.e. the term does preferably not cover food, cosmetics, toothpaste and the like.

Menthol as Antiviral Compound

Surprisingly, the present invention demonstrates that menthol has an antiviral effect. Hence it is also an objective of the present invention to provide methods of reducing the amount of virus in a composition, comprising incubating said composition comprising virus with menthol. It is also an objective of the invention to provide methods of reducing the amount of virus in an individual infection with said virus, comprising administering to said individual a pharmaceutical composition comprising menthol, thereby reducing the amount of said virus in said individual. The invention also relates to uses of menthol for the preparation of a pharmaceutical composition for reduction of virus in an individual in need thereof.

The individual in need thereof may be any individual. Preferably, the individual is an individual infected with one or more of the vira mentioned herein below.

The virus is preferably any of the vira mentioned herein below in the section "Clinical conditions". More preferably, said virus is rhinovirus.

The methods mentioned above may also be combined with administration of one or more other active compounds. In parallel, the pharmaceutical compositions may also comprise one or more other active compounds. Said active compounds may for example be selected from the group consisting of flavonoids, metal complexes and metal salt.

The reduction of virus is preferably a reduction to at the most 80%, more preferably at the most 70%, even more preferably at the most 60%, such as at the most 50%, for example at the most 40%, such as at the most 30%, for example at the most 20%, such as at the most 10% of the initial amount of virus.

More preferably, the reduction of virus results in at least 10%, preferably at least 20%, more preferably at least 30%, for example at least 40%, such as at least 50%, such as at least 60, for example at least 70%, such as at least 80%, for example at least 90% increase in cell survival in an in vitro test system. Cell survival may preferably be determined as for example described in example 2.

Flavonoids

"Flavonoids" useful with the present invention may be any flavonoid known to the person skilled in the art. Flavonoids are polyphenolic compounds isolated from a wide variety of plants with over 4000 individual compounds known. The term "flavonoid" according to the present invention covers both naturally, occurring flavonoids as well as synthetic derivatives thereof. Flavonoids comprise a range of $C_{15}$ aromatic compounds and are found in virtually all land-based green plants.

Preferred flavonoids according to the present invention includes flavonoids of the general formula:

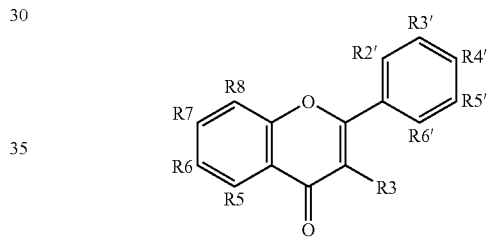

or the general formula:

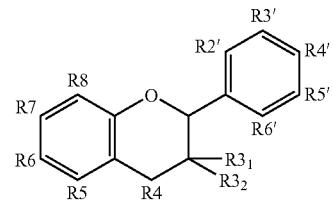

Wherein
R2' can be selected from:
—H
—OH
R3' can be selected from:
—H
—OH
—OCH$_3$
—OCH$_2$CH$_2$OH
R4' can be selected from:
—H
—OH
—OCH$_3$
—OCH$_2$CH$_2$OH R5' can be selected from:
- —H
- —OH
- —OCH$_3$
- —OCH$_2$CH$_2$OH R6' is —H;

R3 including R3$_1$ and R3$_2$ can individually be selected from:
- —H
- —OH
- —O-rutinose
- —O-glucoside
- —O-glucose-p-coumaric acid
- —SOH
- —O-rhamnose R4 can be selected from:
- —H
- —(O)
- —OH R5 can be selected from:
- —H
- —OH
- —O—CH$_2$CH$_2$OH R6 can be selected from:
- —H
- —OH
- —OCH$_3$ R7 can be selected from: —H
- —OH
- —O-glucose
- —OCH$_3$
- —OCH$_2$CH$_2$OH
- —O-glucuronic acid
- —O-rutinose
- —O-rhamnoglucoside R8 can be selected from:
- —H
- —OH Furthermore, flavonoid and/or flavonoid derivatives could be stereoisomers of the above mentioned. Additionally flavonoid and/or flavonoid derivatives could be dimers comprising two flavonoid subunits.

Additionally, flavonoids and/or flavonoid derivatives of the present invention to be used in combination with metal could be any flavonoid and/or flavonoid derivative known to the person skilled in the art. For example such flavonoid and/or flavonoid derivative could be any of the flavonoid and/or flavonoid derivative mentioned in WO 01/03681, which is hereby incorporated in its entirety by reference.

Preferably, the flavonoid and/or flavonoid derivatives are selected from molecules with the above general formulas with the proviso,

| that when R3' is selected from | —OH | —OCH$_3$<br>—OCH$_2$CH$_2$OH |
| --- | --- | --- |
| then R5' is selected from | —H | |
| and when R5' is selected from | —OH | —OCH$_3$<br>—OCH$_2$CH$_2$OH |
| then R3' is selected from | —H | |

Semi-synthetic flavonoids are also within the scope of the present invention. In one embodiment of the invention the flavonoid is a synthetic flavonoid, i.e. a not naturally occurring flavonoid, such as a semi-synthetic flavonoid or a synthetic derivative of a naturally occurring flavonoid.

Preferably, the flavonoid according to the present invention could be selected from the group consisting of: troxerutin, venoruton, hydroxyethylrutosides, hesperitin, naringenin, nobiletin, tangeritin, baicalein, galangin, genistein, quercetin, apigenin, kaempferol, fisetin, rutin, luteolin, chrysin, taxifolin, eriodyctol, catecithin, epicatechin, epigallocatechin, epicatechin gallate, epigallocatechin gallate, flavone, sideritoflavone, hypolaetin-8-O-Gl, oroxindin, 3-hydroxyflavone, morin, quercetagetin-7-O-Gl, tambuletin, gossypin, hipifolin, naringin, leucocyanidol, amentoflavone and derivatives thereof and mixtures thereof.

More preferably, one or more of the R chains are —OCH$_2$CH$_2$OH, yet more preferably, at least two R chains are —OCH$_2$CH$_2$OH, most preferably three R chains are —OCH$_2$CH$_2$OH.

In one embodiment of the invention the flavonoid does not comprise antiviral activity when tested in vitro. Furthermore, it is preferred that said flavonoid is soluble in water.

In a preferred embodiment, at least one flavonoid is a rutoside, more preferably at least one flavonoid is a hydroxyethylrutoside. Even more preferably, all the flavonoids of the composition are rutosides, yet more preferably all the flavonoids of the composition are hydroxyethylrutosides.

For example the pharmaceutical compositions of the invention may comprise a mixture of hydroxyethylrutosides, such as a mixture of mono-, di-, tri- and tetrahydroxyethylrutosides.

In one preferred embodiment the flavonoid derivatives according to the invention comprises a mixture of mono-, di-, tri- and tetrahydroxyethylrutosides. More preferably, the mixture comprise 1% to 15% monohydroxyethylrutoside, such as from 5% to 10% monohydroxyethylrutoside, and from 25% to 50% dihydroxyethylrutoside, such as from 30% to 38% dihydroxyethylrutoside, and from 30% to 70% trihydroxyethylrutoside, such as from 45% to 55% trihydroxyethylrutoside and from 1% to 20% tetrahydroxyethylrutoside, such as from 3% to 12% tetrahydroxyethylrutoside. Most preferably, said mixture of hydroxyethylrutosides is Venoruton.

The flavonoid is most preferably selected from the group consisting of troxerutin, Veneruton, pharmaceutical acceptable salts thereof and functional derivatives thereof.

In one especially preferred embodiment of the present invention at least one flavonoid is troxerutin of the formula:

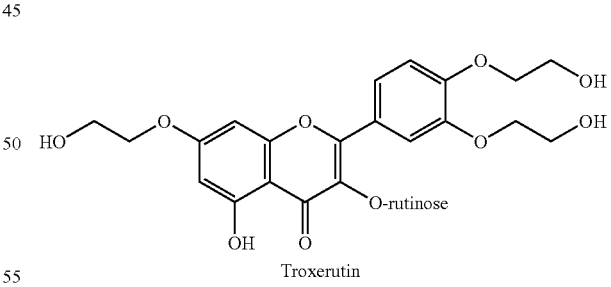

Troxerutin

Troxerutin of the above-mentioned formula is also known as 7,3',4'-tris[O-(2-hydroxyethyl)]rutin (CAS no. 7085-55-4).

The term "Troxerutin" is in the prior art also used to designate a mixture of hydroxyethylrutosides. Hence, the pharmaceutical compositions according to the present invention may also comprise such mixtures of hydroxyethylrutosides (herein designated hydroxyethylrutoside mixture). In preferred embodiments the pharmaceutical compositions comprise no other flavonoids than a hydroxyethylrutoside mixture.

Preferably, the hydroxyethylrutoside mixture comprises at least 40%, for example around 46%, such as at least 50%, for example at least 60%, such as at least 70%, for example at least 80% troxerutin of the above-mentioned formula. The hydroxyehtylrutoside mixture may also comprise in the range of 2 to 10%, more preferably in the range of 3 to 7%, even more preferably around 5% monohydroxyehtylrutosides. The hydroxyehtylrutoside mixture may also comprise in the range of 20 to 50%, more preferably in the range of 30 to 40%, even more preferably around 34% dihydroxyehtylrutosides. The hydroxyehtylrutoside mixture may also comprise in the range of 2 to 10%, more preferably in the range of 3 to 7%, even more preferably around 5% tetrahydroxyehtylrutosides. Other hydroxyethylated components, such as hydroxyehtylated quercetin, for example tetrahydroxylated quercetin may be present in small quantities.

In one embodiment of the invention some or all of the flavonoids are aglycones. For example, at least one flavonoid may be a rutoside aglycone, preferably at least one flavonoid is a hydroxyethythyrutoside aglycone, more preferably, at least one flavonoid is troxerutin aglycone.

Aglycones are flavonoids from which at least one sugar group has been removed. Aglycones may be prepared using any suitable mechanism, for example by the aid of β-glucoronidase (see also Shimoi et al., 2001).

The chemical formula of troxerutin aglycone is shown below:

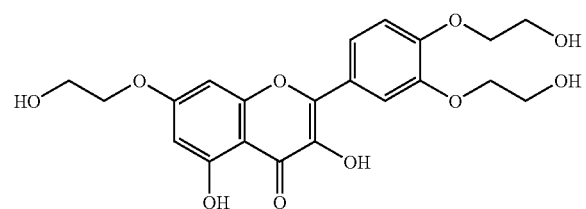

In one embodiment of the invention at least some of the flavonoids, such as essentially all flavonoids are present as metal chelates, such as chelates of iron(III), iron (II), copper (II) or zinc(II). Preferably flavonoids may be present as chelates of $Zn^{2+}$. Metal chelation of polyphenols is for example described in (Hider et al., 2001) and the flavonoid metalchelate may for example be formed by any of the mechanisms described therein. Preferably, the flavonoid metal chelate is $Zn^{2+}$/troxerutin or $Zn^{2+}$/Veneruton.

The pharmaceutical compositions according to the present invention may also comprise mixtures of more than one flavonoid. For example-such a mixture may comprise 2, such as 3, for example 4, such as 5, for example 6, such as 7, for example 8, such as 9, for example 10, such as more than 10 different flavonoids. Preferably, such a mixture comprise 8 to 10 different flavonoids.

In one embodiment of the invention the flavonoid is not astragalin.

Clinical Conditions

The present invention relates to uses of flavonoids and menthol for the preparation of a medicament for the treatment of a clinical condition. The invention also relates to methods of treatment of a clinical condition. The-clinical condition may be any clinical condition, which may be treated using flavonoids and menthol.

However, in preferred embodiments of the present invention the clinical conditions is a condition relating to common cold, such as common cold of the upper and/or lower respiratory tract and/or eyes. Conditions relating to common cold comprises common cold, a viral infection and/or a bacterial infection of the upper and/or lower respiratory tract and/or eyes, rhinitis, an allergic condition having one or more symptoms similar with the symptoms of a common cold for example allergic rhinitis initiated by rhinovirus infection, asthma like exacerbations and/or other abnormal airway functions derived from various dysfunctions of the immune system, such as for example hay fever or the like.

Furthermore, conditions relating to a common cold may comprise secondary bacterial infection(s) that follow soon after a primary viral infection. Secondary bacterial infections may for example be initiated by the normal bacterial flora present in the upper and/or lower respiratory tract and/or eyes.

Symptoms of conditions relating to common cold can be selected from the group comprising, but is not limited to: coughing, sneezing, muscle pain, sore throat, hoarseness, irritated throat, headache, malaise, chilliness, nasal discharge, nasal obstruction, pain relating to the sinuses, fever, rhinitis, swelling of mucosal membranes, pharyngitis, asthma, and acute as well as chronic bronchitis.

In the present invention the upper respiratory tract includes the mouth, nose, sinuses, throat, and the respiratory tract to epiglottis. The lower respiratory tract includes the rest of the bronchial tree including the bronchioles and lung vacuoles.

The invention also relates to the treatment of eye symptoms related to the condition of the respiratory tract in that the condition may involve the mucosal lining of the respiratory tract as well of the eyes. By the term treatment as used herein is also meant prevention of symptoms whether the prevention is in fact a decrease in the development of symptoms or a prevention of the symptoms to arise in first place, e.g. upon exposure to infection.

According to the present invention a pharmaceutically effective amount or a therapeutically effective amount is to be understood as an amount sufficient to induce a desired biological result. The result can be alleviation of the signs, symptoms, or causes of a disease, for example of common cold, preferably, the result is a significant alleviation of signs, symptoms or causes of common cold. For example, an effective amount is generally that which provides either subjective relief of symptoms or an objectively identifiable improvement as noted by the clinician or other qualified observer, preferably such a relief of symptoms is a significant relief. The relief may for example be evaluated based on a symptom score as disclosed herein in the examples. Accordingly, effective amounts can vary widely depending on the individual, on the disease or symptom to be treated.

Most common cold patients produce interferon following infection of the respiratory tract (Cate et al., 1969), which per se in principle should be sufficient to alleviate the infection.

Hence, in one preferred aspect of the present invention the treatment of a viral infection is not to be regarded as a direct antiviral effect but as a modification or inhibition of cytokines or other factors relevant for the establishment or continuation of a viral infection located in the mucosal membrane of the respiratory tract or eyes. Furthermore, the treatment preferably inhibits inflammation processes in the mucosal membrane of the respiratory tract or eyes and thereby alleviates symptoms of common cold. Accordingly, the invention relates-to use of a flavonoid and menthol for the treatment of symptoms of viral infection of the upper and/or lower respiratory tract and/or eyes, wherein the flavonoid and/or flavonoid derivative has no-antiviral effect in vitro.

Thus, in one embodiment of the present invention the flavonoid does not comprise an antiviral or anti bacterial effect in vitro. In vitro antiviral and/or antibacterial effect can be determined in various laboratory tests. Preferably, such laboratory tests comprise a cultured cell line capable of being infected with the bacteria or virus to be tested as well as said bacteria or virus. More preferably, said cultured cell line is WISH cells and said virus is a rhinovirus selected from the group consisting of: rhinovirus 1A, rhinovirus 15 and rhinovirus 39. Most preferably antiviral effect is determined using the MTS method as described in example 1. When antiviral effect is measured according to the MTS method as described in example 1, a protection of less than 10%, preferably less than 7.5%, more preferably less than 5%, even more preferably less than 3%, most preferably less than 2% is to be regarded as no antiviral effect in vitro.

Preferably, the effect of the flavonoid and/or flavonoid derivative is closely related to the living organism such as the effect is a modulatory effect on specific factors and biological reactions related to the affected mucosal membrane. The precise mechanisms are currently not known.

Very often common cold is initiated by, associated with or followed by a viral infection, which is involved in the common cold or symptoms of the common cold. In one embodiment of the present invention the condition relating to common cold is associated with a viral infection of the upper and/or lower respiratory tract and/or eyes.

The virus infection which a common cold is most often associated with or initiated by, is infection by one or more virus selected from the group consisting of: adenoviruses, parvoviruses, picornaviruses, reoviruses, orthomyxoviruses, paramyxoviruses, arenaviruses, caliciviruses, coronaviruses, orthomyxoviruses, rhinovirus, influenza virus, including influenza virus type A and B, echovirus, respiratory syncytial virus (RSV), and coxsackie virus. Rhinovirus is the most common virus identified in relation to common cold. The term rhinovirus is meant to comprise any rhinovirus for example any of the rhinoviruses 1-113. However, very often the above virus may be present in individuals with no symptoms of common cold. Preferably, the virus infection associated with common cold according to the present invention is infection by rhinovirus or coronavirus.

Very often the common cold is associated with or followed by a bacterial infection, which is involved in the common cold or symptoms of the common cold. Such a bacterial infection may in one embodiment of the present invention be a secondary infection following a primary infection with for example a virus. In one embodiment of the present invention the condition relating to common cold is associated with a bacterial infection of the upper and/or lower respiratory tract and/or eyes.

The bacterial infection, which may be associated with a common cold or with the symptoms thereof is most often infection by one or more bacteria selected from *Streptococcus pneumoniae, Streptococcus Haemolyticae, Haemophilus influenzae,* and *Moraxella catarrhalis.*

Furthermore, common cold may be initiated by a microbial infection. Such a microbial infection may lead to similar inflammatory responses as viral infections involving the same effector cells for example neutrophiles. Accordingly, such microbial infections may be treated in a fashion similar to viral infections associated with common cold.

Many allergic reactions are associated with symptoms similar to the symptoms of a common cold and it has surprisingly been shown that such symptoms of an allergic disorder may also be effectively treated by the method and use as disclosed herein. Hence, in one embodiment of the present invention the condition relating to common cold is an allergic disorder.

The allergic conditions according to the present invention is preferably selected from rhinitis, asthma, acute and chronic bronchitis, and hay fewer. The most common symptoms in relation to allergies are one or more symptoms selected from nasal discharge, nasal congestion, sneezing, cough, swelling of mucosal membranes, rhinitis. More preferably, the allergic condition according to the present invention is selected from the group consisting of rhinitis and hay fewer. In a further aspect of the present invention the individual may have relief from the symptoms based on a decreasing effect of said flavonoid on the mucosal swelling associated with the infection or condition mentioned herein. In a still further aspect the present invention encompass acute allergic reactions related to insect bites and sticks and in a still further aspect to the allergic reactions from food or other allergens leading to swelling of the mucosa of the mouth and/or throat in such acute reactions.

It is furthermore contained within the present invention to treat allergic conditions that is initiated by one or more agents selected from the group consisting of: pollution, house dust, common dust mite such as *Dermatophagoides Farinae* or *Dermatophagoides Pteronyssinus,* pollen such as grass pollen, tree pollen or weed pollen, mold, animal danders or feathers, fungal spores and chronic inhalation of for example, wheat flour.

Accordingly, the conditions related to common cold of the present invention could be an infection or common cold or allergic condition characterised by one or more symptoms selected from the group comprising: coughing, sneezing, muscle pain, sore throat, hoarseness, irritated throat, headache, malaise, chilliness, nasal discharge, nasal obstruction, pain relating to the sinuses, rhinitis, swelling of mucosal membranes, pharyngitis, asthma, and acute as well as chronic bronchitis.

When the condition relating to common cold is an allergic condition, preferably such a condition is treated by administration of flavonoid and menthol without simultaneous administration of metal to the individual in need thereof. More preferably said flavonoid is selected from the group consisting of troxerutin and Veneruton®.

The classical common cold results in symptoms, which lasts for approximately one week. However, in certain cases conditions relating to common cold results in symptoms, which lasts for much longer. Such long lasting common colds for example last for more than 10 days, such as more than 2 weeks, such as more than 3 weeks, for example more than one month, such as more than 6 weeks. Individual suffering from long lasting common cold are preferably treated by administration of flavonoid and menthol without simultaneous administration of metal. More preferably said flavonoid is selected from the group consisting of troxerutin and Veneruton®.

In contrast, individuals suffering from a classical common cold wherein treatment is initiated 1 to 5 days following the onset of common cold symptoms, preferably 1 to 3 days following the onset of common cold symptoms may be treated by administration of both a flavonoid, menthol and metal according to the present invention.

Metal Complexes and Metal Salts

In one embodiment of the invention the pharmaceutical compositions comprises flavonoid, menthol and a metal complex and/or metal salt.

The metal according to the present invention is preferably selected from the group consisting of zinc, manganese, cadmium, cobalt, iron and selenium. The metal may for example be in the form of $Zn^{2+}$, $Mn^{2+}$, $Cd^{2+}$, $Co^{2+}$, $Fe^{2+}$ and $Se^{2+}$. Most preferably the metal is zinc. Preferably zinc is $Zn^{2+}$, given in the form of a salt and/or complex or derivatives thereof.

Within the scope of the present invention, zinc could be in any suitable form for example as ZnGluconate, as $Zn(acetate)_2$, as $Zn^{2+}$ aminochelates, as $Zn^{2+}$ amino acid chelates, as $Zn^{2+}$ DL-methionine, as $Zn^{2+}$ L-methionine, as histidine derivatives or as a complex with amino acids in combination with histidine, or the like such as for example PolaPreZinc®. Furthermore zinc could be in the form of zinc sulfate, zinc chloride, Nitric-acid zinc, phosphoric-acid zinc, ulmin acid zinc, zinc fluoride, zinc iodide, a zinc hydroxide, zinc carbonate, a zinc chromate, benzoic-acid zinc, zinc acetate, p-aminobenzoic-acid zinc, p-dimethylamino benzoic-acid zinc, p-zinc phenolsulfonate, p-methoxy cinnamic-acid zinc, lactic-acid zinc, gluconic-acid zinc, citric-acid zinc, salicylic-acid zinc, a zinc stearate, lauric-acid zinc, myristic-acid zinc, Oleic-acid zinc, 2,5-pyridine dicarboxylic-acid zinc, 2,6-pyridine dicarboxylic-acid zinc, 4-pyridine dicarboxylic-acid zinc, 2,4-dicarboxy pyridine zinc, 3-hydroxy-2-carboxy pyridine zinc, 3-n-propoxy-2-carboxy pyridine zinc, 3-n-hexyloxy-2-carboxy pyridine zinc, 5-n-propoxy-2-carboxy pyridine zinc, 5-n-butoxy-2-carboxy pyridine zinc, 5-(2-ethyl-hexyloxy)-2-carboxy pyridine zinc, 6-n-butoxy-2-carboxy pyridine zinc, 3-methoxy-2-carboxy pyridine zinc, 5-methoxy-2-carboxy pyridine zinc, 6-methoxy-2-carboxy pyridine zinc, 6-n-hexyloxy-2-carboxy pyridine zinc, 3methyl-2-carboxy pyridine zinc, 4-methyl-2-carboxy pyridine zinc, 4-tert-butyl-2-carboxy pyridine zinc, 5-methyl-2-carboxy pyridine zinc, 5-n-hexyl-2-carboxy pyridine zinc, 3-n-undecyl-2-carboxy pyridine zinc, 4-n-undecyl-2-carboxy pyridine zinc, 5n-butyl-2-carboxy pyridine zinc, 6-n-undecyl-2-carboxy pyridine zinc, 4nitroglycerine-2-carboxy pyridine zinc, 5-hydroxy-2-carboxy pyridine zinc, 4fluoro-2-arboxy pyridine zinc, 2-carboxy pyridine N-oxide zinc, picolinic-acid zinc, Nicotnic-acid zinc, nicotinamide zinc, 3,4-dihydroxy benzoic-acid zinc, Screw histidine zinc, hinokitiol zinc, protoporphyrin zinc, porphyrin zinc or picolinic-acid amide zinc.

It is contained within the present invention that zinc could be a combination of the above mentioned zinc salts and/or a zinc complexes. Such combination could comprise two or more sorts. Preferably zinc is selected from the group consisting of $Zn^{2+}$ aminochelates, $Zn^{2+}$ amino acid chelates, $Zn(acetate)_2$, $Zn^{2+}$ DL-methionine, $Zn^{2+}$ L-methionine, ZnGluconate and PolaPreZinc®. Preferably, zinc is in the form of ZnGluconate or PolaPreZinc®.

Administration, Formulation and Effect

In one aspect the present invention relates to methods of treatment involving administration of any of the pharmaceutical compositions described herein above. The invention also relates to use of flavonoid(s) for the preparation of a medicament for the treatment of a clinical condition, such as common cold. Said medicament is preferably free of all compounds of peppermint oil except menthol. In one embodiment the invention relates to use of flavonoid and menthol for the preparation of a medicament for treatment of a clinical condition, such as common cold (see herein above).

The pharmaceutical compositions according to the present invention should preferably comprise an effective dosage of flavonoids and menthol and optionally of metal. It is contained within the present invention that the effective dosage is distributed over several dosage units. By way of example, if the pharmaceutical composition is formulated as lozenges, then the daily effective dosage may be distributed in 2 to 20 lozenges.

It is also contained within the present invention that flavonoids and menthol are formulated individually, and that the pharmaceutical composition thus comprises two individual formulations, which may be administered simultaneously or sequentially in any order. However, preferably they are administered simultaneously.

The effective dosage of flavonoids may vary according to the individual in need thereof and to the particular clinical condition. In general, the effective will be in the range of from 5 to 5000 mg daily. More preferably, the effective dosage is in the range of from 10 mg to 4000 mg, such as in the range of from 30 mg to 3000 mg, even more preferably in the range of from 40 mg to 2000 mg daily, yet more preferably, in the range of from 50 mg to 1000 mg daily.

Furthermore, the effective dosage of said flavonoids could be a dosage equivalent of a dosage of troxerutin of from 5 mg to 5000 mg daily.

The effective dosage of Venoruton or troxerutin or a hydroxyethylrutoside mixture or a pharmaceutically acceptable salt or a functional derivative or a metal chelat thereof is normally in the range of from 5 to 5000 mg. In general the effective dosage is in the range of from 10 mg to 4000 mg, such as in the range of from 30 mg to 3000 mg, preferably in the range of from 40 mg to 2000 mg daily, more preferably, from in the range of 50 mg to 1000 mg daily, yet more preferably in the range of from 50 to 500 mg daily, most preferably in the range of from 100 to 300 mg daily for example an adult human being.

The effective dosage of menthol is depending on the individual to be treated in general in the range of 1 mg to 200 mg daily. Preferably, the effective dosage of menthol is in the range of 5 mg to 100 mg daily, more preferably the effective dosage is in the range of 10 mg to 50 mg daily, even more preferably the effective dosage is in the range of 15 mg to 40 mg daily, yet more preferably the effective dosage is in the range of 20 mg to 35 mg daily for for example an adult human being.

The administration of flavonoids and menthol according to the present invention is preferably a very frequent administration during the day. If menthol and flavonoid are formulated individually, the administration frequency may differ for flavonoid and menthol, respectively. Accordingly, the daily dosage may individually be administered in divided dosages of 1 to 36 individual dosages daily, preferably 2 to 24 times daily, more preferably 3 to 12 times daily, such as 5 to 8 times daily, for example around 6 times daily. Preferably, the first 2 doses are administrated simultaneously. The specific number of daily applications may be correlated to the individual way of administration and the severity of the symptom in question. The preferred treatment is a treatment where the medicament is present in the mucosal membrane as constant as possible due to the theory that the individual factors involved in the maintenance of the symptoms are constantly produced in the affected mucosal membrane during the illness.

In one embodiment the pharmaceutical compositions comprising flavonoids and menthol according to the present invention are administrated in combination with a second treatment such as in combination with an antiviral treatment including treatment against influenza such as TaMiFlu®, treatment against rhinitis such as Picovir®; or treatment with antibodies against streptococcus; or treatment with interferons (alpha, beta or gamma) and mixtures thereof. The antiviral agents include TamiFlu or other neuraminidase inhibitors or rimantadine or antibodies against RSV. The second treatment may also be a metal complex or metal salt (see herein above).

In another embodiment of the present invention the second treatment is administration of an anti-microbial agent. Preferably, the anti-microbial agent is distinct and specific, however the anti-microbial agent may also be a general antibiotic. In particular, an anti-microbial agent may be administrated to treat conditions associated with bacterial infections.

The effective dosage of metal complex or metal salt depends on the particular metal complex or metal salt and the clinical condition to be treated. In general, however in the range of 0.1 mg to 1000 g metal is adminstrated daily. Preferably the metal is zinc. The effective dosage of Zinc depends upon the form of zinc component which is adminstrated. Preferably between 0.1 mg and 500 mg $Zn^{2+}$ is administrated, such as between 0.5 mg and 250 mg, for example between 1 mg and 150 mg, such as between 5 mg and 100 mg, for example between 10 mg and 50 mg per dose. If the zinc compound is ZnGluconate, preferably between 5 mg and 1000 mg, more preferably between 10 mg and 500 mg, even more preferably between 10 mg and 100 mg, yet more preferably between 20 mg and 80 mg, even more preferably between 30 mg and 70 mg, most preferably around 50 mg ZnGluconate is administrated per dose. If-the zinc compound is PolaPreZinc, preferably between 1 mg and 500 mg, more preferably between 5 mg and 250 mg, even more preferably between 10 mg and 100 mg, most preferably around 25 mg.

The administration of a flavonoid, menthol and metal salt and/or metal complex may be either simultaneously as separate or combined formulations or it may be sequential in any order.

It is preferred to present flavonoids and/or menthol and/or metals according to the present invention in the form of a pharmaceutical formulation. Accordingly, the present invention further provides pharmaceutical formulations, either as a single composition or as a kit of parts, for medicinal application, which comprises a flavonoid and menthol as well and optionally a metal salt and/or metal complex according to the present invention or a pharmaceutically acceptable salts thereof, as herein defined, and a pharmaceutically acceptable excipient therefore.

The pharmaceutical formulations according to the present invention may be prepared by conventional techniques, e.g. as described in Remington: The Science and Practice of Pharmacy 1995, edited by E. W. Martin, Mack Publishing Company, 19th edition, Easton, Pa. The phamaceutical formulation may have any form known to the person skilled in the art. For example the pharmaceutical formulation may be in the form of a solution, dispersion, emulsion, suspension, bioadhesive and non-bioadhesive gel, powder, micropheres, tablets, lozenges, chewing tablets, chewing gum, pills, capsules, cachets, suppositories, dispersible granules, drops, sprays, aerosols, insufflators, inhalators, patches, a lollipop, ointment, lotion, cream, foam, implant, syrup or balm. The skilled person may select the appropriate administration form based on the common knowledge within the field of delivery systems for pharmaceuticals.

It is believed that the optimal effect is obtained by a direct topical application of the flavonoids and menthol according to the present invention on the mucosal membrane in question. Accordingly, it is preferred that the administration is topical administration directly to the mucosal membrane, more preferably, to the-mucosal membrane of the upper and/or lower respiratory tract and/or of the eyes, even more preferably the mucosal membrane of the oral cavity. The formulation should generally be distributed to a major part of the mucosal involved in the specific condition or symptom to be treated.

In a preferred embodiment of the invention the pharmaceutical composition is useful for oral administration. Hence, it is preferred that the pharmaceutical composition is selected from the group consisting of lozenges, troches, capsules, syrups, tablets, lollipops, solutions, dispersions, suspensions, powders, micropheres, chewing tablets, chewing gums, sprays and pills.

It is also preferred within the present invention that the pharmaceutical composition is a slow-release composition, i.e. that the release of active ingredients of the composition lasts for for example 1 min to 24 hours, such as for 1 min to 12 hours, for example from 1 min. to 6 hours, such as from 1 min to 1 hour.

In a preferred embodiment of the invention the pharmaceutical composition is lozenges.

The pharmaceutical composition according to the present invention usually comprise pharmaceutically acceptable excipients, which can be either solid or liquid. Preferably, such pharmaceutically acceptable excipients are not therapeutically active ingredient, but rather said excipients may be one or more substances which may act as diluents, flavouring agents, solubilisers, lubricants, suspending agents, binders, preservatives, wetting agents, tablet disintegrating agents, or an encapsulating material. Such excipients include pharmaceutical grades of mannitol, lactose, starch, magnesium stearate, sodium saccharine, talcum, cellulose, glucose, lactose, pectin, dextrin, starch, gelatin, sucrose, magnesium carbonate, tragacanth, methylcellulose, sodium carboxymethylcellulose, a low melting wax, cocoa buffer, and the like. Menthol is not regarded an excipient wihtin the meaning of the present invention. Preferably, at least one pharmaceutically acceptable excipient is Magnesium stearate. In addition, the pharmaceutical acceptable excipients may be colorants, flavours, stabilisers, buffers, artificial and natural sweeteners, dispersants, thickeners, solubilising agents, and the like.

In powders, the excipient is preferably a finely divided solid, which is a mixture with the finely divided active components. In tablets, the active components are mixed with the excipient having the necessary binding capacity in suitable proportions and compacted in the shape and size desired. The powders and tablets preferably contains from one to about seventy percent of the active-compound.

Formulations suitable for topical administration in the mouth include lozenges comprising active agents in a flavoured base, usually sucrose and acacia or tragacanth; pastilles comprising the active ingredient in an inert base such as gelatin and/or glycerin and/or sucrose and/or acacia; and mouthwashes comprising the active ingredient in a suitable liquid carrier. In one preferred embodiment the lozenges comprise sorbitol.

The compounds of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Surprisingly, the present invention discloses that even though common cold is usually caused by an infection of the upper and/or lower respiratory tract, it can be treated effectively by topical administration directly to the mucosal membrane of the oral cavity. Since administration directly to the mucosal membrane of the oral cavity is very convenient for the individual to be treated, it is a considerable advantage of the present invention that administration can be performed directly to said mucosal membrane. In addition, the present invention discloses that allergic rhinitis also can be treated by applying the compounds according to the present invention directly to the musocal membrane of the oral cavity. Accordingly, the compounds according to the present invention are preferably formulated as lozenges, chewing tablets, chewing gum, drops, sprays and aerosols, which can be applied directly to the mucosal membrane of the oral cavity. Most preferably, the compounds according to the present invention are formulated as lozenges, which can be directly applied to the mucosal membrane of the oral cavity.

The individual in need of a treatment according to the invention could be any individual, however preferably, such individual is a human being. The individual will generally have a score relating to symptoms based on the score system as disclosed in Patients diary, (see examples) of at least 4 to 5, such as at least 6, preferably, at least 10, more preferably the patient would have a score of at least 15, whereas an individual with a score of 3 or less is not to be regarded as sick. Generally speaking a score around 5 to 6 or lower will allow the person to continue his/her work.

In a further aspect of the invention, the treatment results in a decrease in the severity of symptoms corresponding to a decrease of score as measured according to patients diary herein of at least 15% within 24 hours, such as least 25%, .more preferably of at least 30% in 24 hours from the start of the treatment. After 48 hours of treatment the scores is preferably decreased with at least 20% in 48 hours, such as with at least 30%, for example with around 40% to 60%, more preferably with at least 40%, yet more preferably with at least 50%, even more preferably with at least 60%, yet more preferably at least 70%, even more preferably at least 75% in 48 hours from the start of the treatment. 72 hours of treatment preferably results in a decrease of score as measured according to Patients Diary herein of at least 30%, preferably at least 40%, more preferably at least 50%, even more preferably at least 55%, yet more preferably at least 59%, even more preferably at least 65%, yet more preferably at least 70%, even more preferably at least 80%, yet more preferably at least 85%, even more preferably at least 90% in 72 hours from the start of the treatment. However, the preferred decrease in symptom score is dependent on the condition relating to common cold to be. treated, the scheme of treatment and the individual patient.

It is in particularly preferred that at least one symptom, preferably at least 2 symptoms, more preferably at least 3 symptoms selected from the group consisting of clogged nose, rhinorrhea, coughing, headache, sneezing and sore throat are essentially eliminated after 72 hours of treatment.

Flavonoids are known to possess anti-oxidative properties, and according to one further aspect, the flavonoid is a flavonoid having a singlet Oxygen Quenching measured as the rate constant of $O_2$ quenching K of from $10^4$ to $10^9$ $M^{-1}$ $s^{-1}$. Preferably, the rate is $10^4$ to $10^8$ $M^{-1}$ $s^{-1}$. The singlet oxygen quenching can be measured using a variety of solvents known to the person skilled in the art. Preferably, the solvent is selected from the group consisting of $CD_3OD$, a mixture of $CCl_4$ and $CH_3OH$ of 1:3 and $CH_3CN$.

EXAMPLES

Example 1

Methods

Virus Titrations

Rhinovirus 1A, rhinovirus 15 and rhinovirus 39 were titrated according to the tetrazolium salt (MTS)-method (Berg et al., 1990) (Hansen et al., 1989)). WISH cells were seeded in a micro tray at 3000 cells per well and incubated at 37° C., 5% $CO_2$ overnight; the following morning the medium was replaced with 10-fold dilutions of either rhinovirus 1A, rhinovirus 15 or rhinovirus 39, respectively, in fresh medium and the trays were incubated 4-5 days at 33° C.; a microscopical examination confirmed that the CytoPathogenic Effect (CPE) was fully developed (CPE equal to 100%). The minimal amount of virus (i.e.: the highest dilution of the virus in question) which produced 100% destruction was used as "challenge virus" in the subsequent experiments. To quantitate the CPE in terms of % destruction, MTS (Berg and Owen, 2003) was added to all cultures and after 3 h incubation at 37° C. (without $CO_2$) the trays were read in a scanner as previuosly described (Berg et al., 1990). Control cell cultures, that were not infected with virus, were included in the experiment; the latter gave the highest OD as these cells were not damaged; depending on the concentration of virus added to the different wells, the $OD_{492}$ varied, accordingly: 100% CPE yielded a low OD(<0.200); 0% CPE corresponding to no infection at all (controls cell) gave a high OD (>1.200).

Interferon Titration

Interferon titration was performed as follows (cf. Berg et al., 1990): 3.000 WISH cells were seeded in a microtray and on the following morning, the medium was replaced with 2-fold dilutions (from a 0-30 units/ml stock solution) of HuIFN-α-2b (Intron A) in fresh medium comprising 2% serum. After incubation overnight, the medium was replaced with fresh medium comprising challenge virus and incubated at 33° C., 5% $CO_2$ for 3-5 days and processed further as described in Example 2.

Example 2

FIGS. 1A, 1B, 2A, and 2B

Experiment: 1 g pure Menthol(-) from Sigma was dissolved into 3 ml 100% Ethanol and kept at 4° C. (Menthol stock solution). Japanese peppermint oil (PPO) was produced each time from the bottle(stored at 4° C. from the supplier (local hospital pharmacy(RH)). The two stock solutions were used at dilutions (final) as indicated in the text/figures.

Figure 1B:
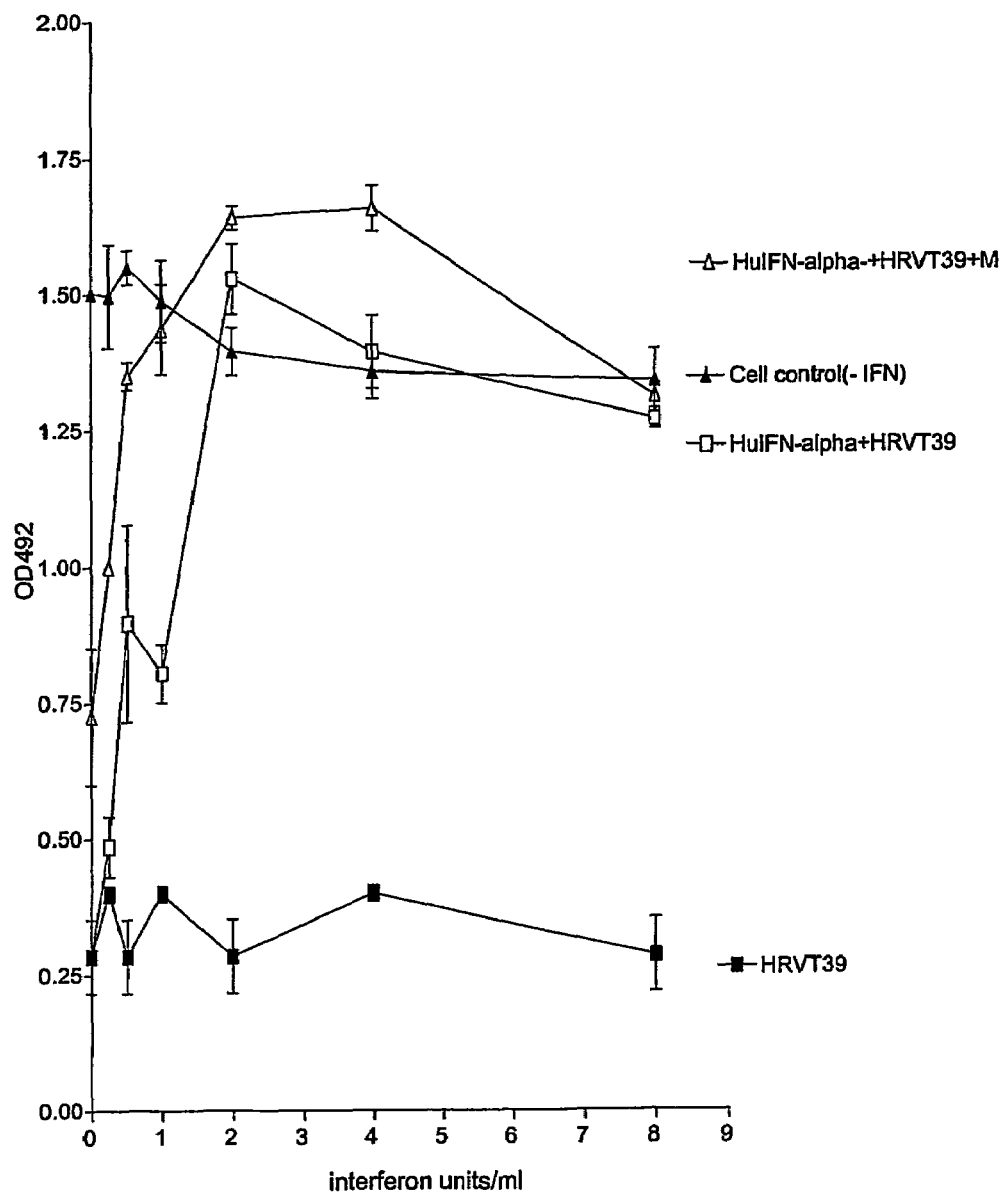
FIG. 1B illustrates the antiviral activity of natural HuIFN-α (designated HuIFN-alpha) versus rhinovirus-T39 at a dilution of $10^{-2,5}$ (designated HRV T39) in the presence and absence of menthol (1:800) (designated M).

1:800 dilutions of Menthol(-) were added to interferon dilutions on confluent monolayer cultures yielding the interferon units/ml as indicated in FIGS. 1A and 1B and rhinovirus, RHV-T-39 was added at $10^{-2}$ dilution (FIG. 1A) or $10^{-2,5}$ (FIG. 1B) diluted from a virus stock preparation of RHV-39 and the cells were incubated at 33° C. for 3-4 days until control cultures infected with the virus alone yielded 100% destruction as seen in a microscope; at that time MTS (3-[4, 5-dimethylthiazol-2-yl]-5-[3-carboxymethyloxyphenyl]-2 [4-sulphonyl]-2H-tetrazolium)/PMS (phenazine methosulfate) was added and the dehydrogenase in the intact cells produced a color which subsequently was measured in an ELISA scanner as previously described(Hansen et al., 1989; Berg et al., 1990). The results were graphed with the concentration of interferon on the horizontal scale and the $OD_{492}$ readings on the vertical scale.

Results: The lower curve (RHVT39 in FIG. 1a) illustrates the variation of the virus infection in the individual wells. As can be seen the OD-level is around 0.15 corresponding to a 50-fold reduction in the signal compared to non-infected control cell (black triangle: Cell control(-IFN)); upper curve).

Conclusion: The presence of Menthol yields a significant protection amounting to 10-15% compared to uninfected control cells(cf. protection levels at IFN=0 units/ml);

At the interferon range between 0 and 8 units/ml the interferon curve+menthol is significantly above the interferon curve, demonstrating a specific potentiation.

Similar results are also seen at a lower virus concentration ($10^{-2,5}$—FIG. 1b).

Figure 2A:
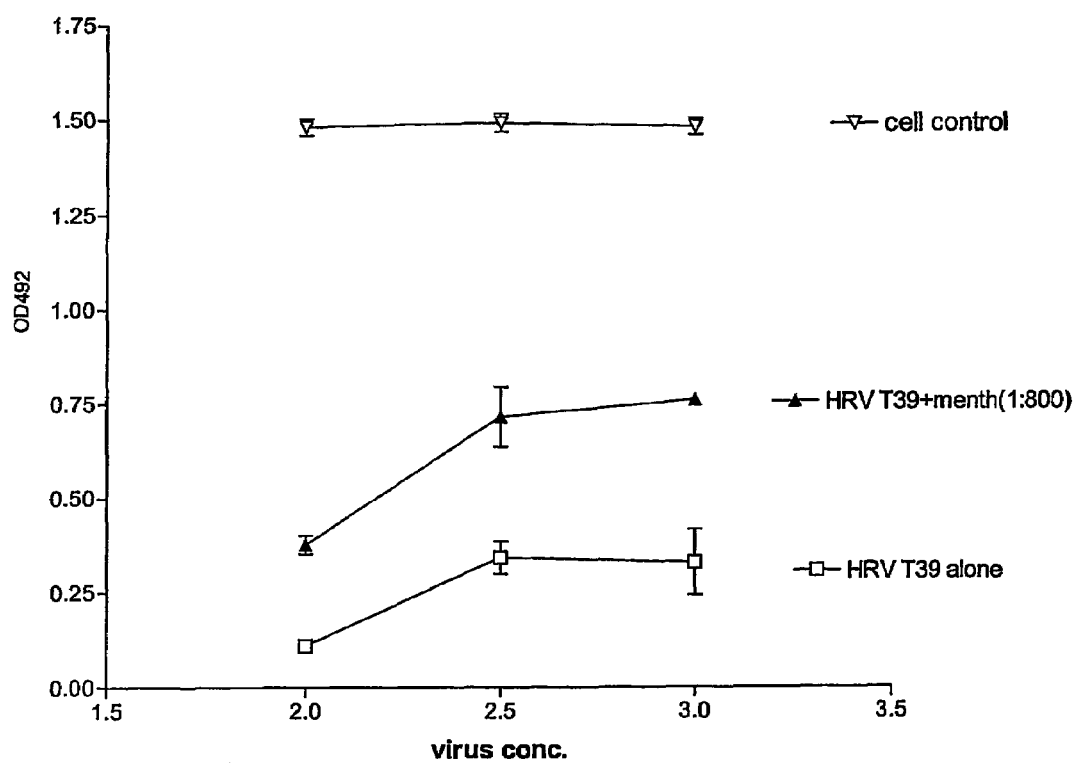
FIG. 2A illustrates the antiviral activity of Menthol at a dilution of 1:800 (designated menth) versus rhinovirus T39 (designated HRV T39).
Figure 2B:
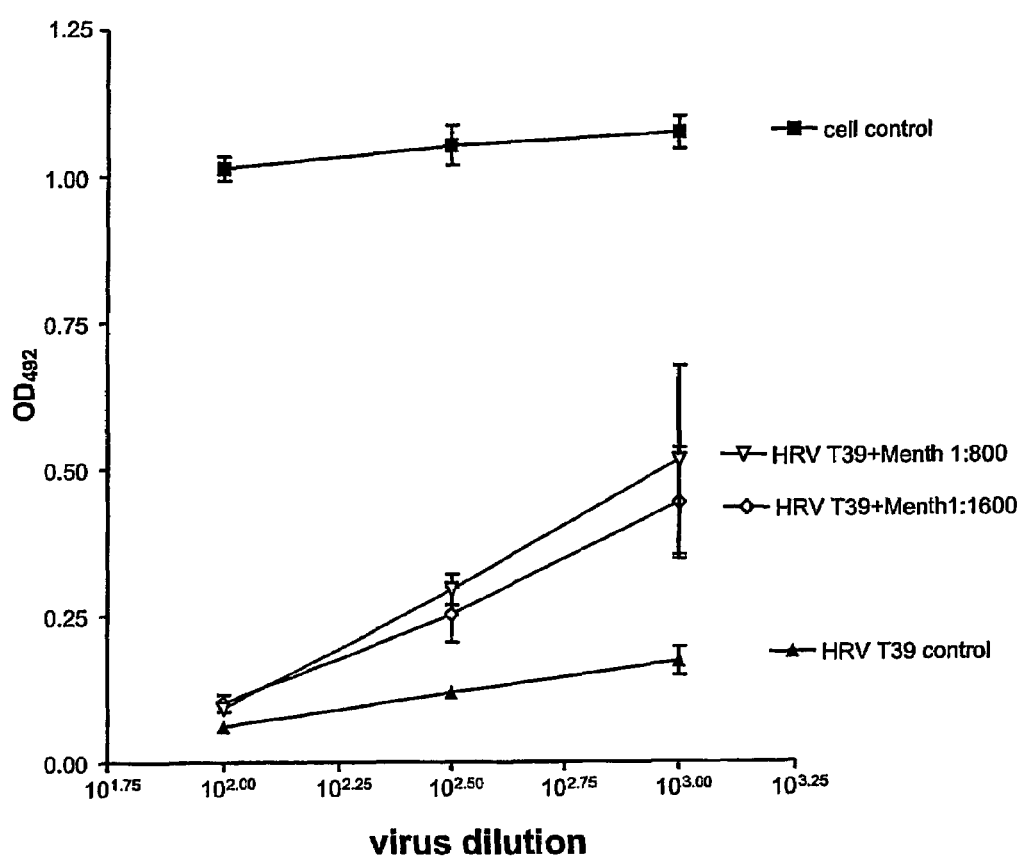
FIG. 2B illustrates the antiviral action of menthol (designated Menth) at dilutions 1:800 and 1:1600 versus rhinovirus T39 (designated HRV T39).

To further elucidate the action of menthol on the growth of human rhinoviruses the following experiments was performed: monolayers of WISH cells in microtrays were titrated with rhinoviruses in the presence or absence of menthol at various dilutions, respectively, cf. FIG. 2A: At a dilution of 1:800 (made from the menthol stock solution described above) there was a significant increase in the protection as the menthol curve is located at a significant higher level at the dilution range of the virus ($10^2$-$10^3$), corresponding roughly to a 50% increase in protection compared to virus controls receiving no menthol, at all. This finding was reproducibly found, cf. for example FIG. 2B displaying similar result from a subsequent experiment. The protection was seen with all three rhinoviruses employed (RHV 1A, 17, and 39A), cf. (Berg et al., 2003)

Conclusion of FIGS. 1A -2B: The above described experiments demonstrate that menthol has a direct effect on the growth of rhinoviruses, per se, and thus can be considered to exert antiviral activity in man infected with rhinoviruses or other related upper respiratory viruses known to induce the common cold syndromes. Furthermore, it also indicates that the natural interferon system, known to be activated in man during common cold infections (Cate et al., 1969), can be potentiated further, much in the same way as described recently by Berg et al. (Berg et al., 2001).

Example 3

Figure 3A:
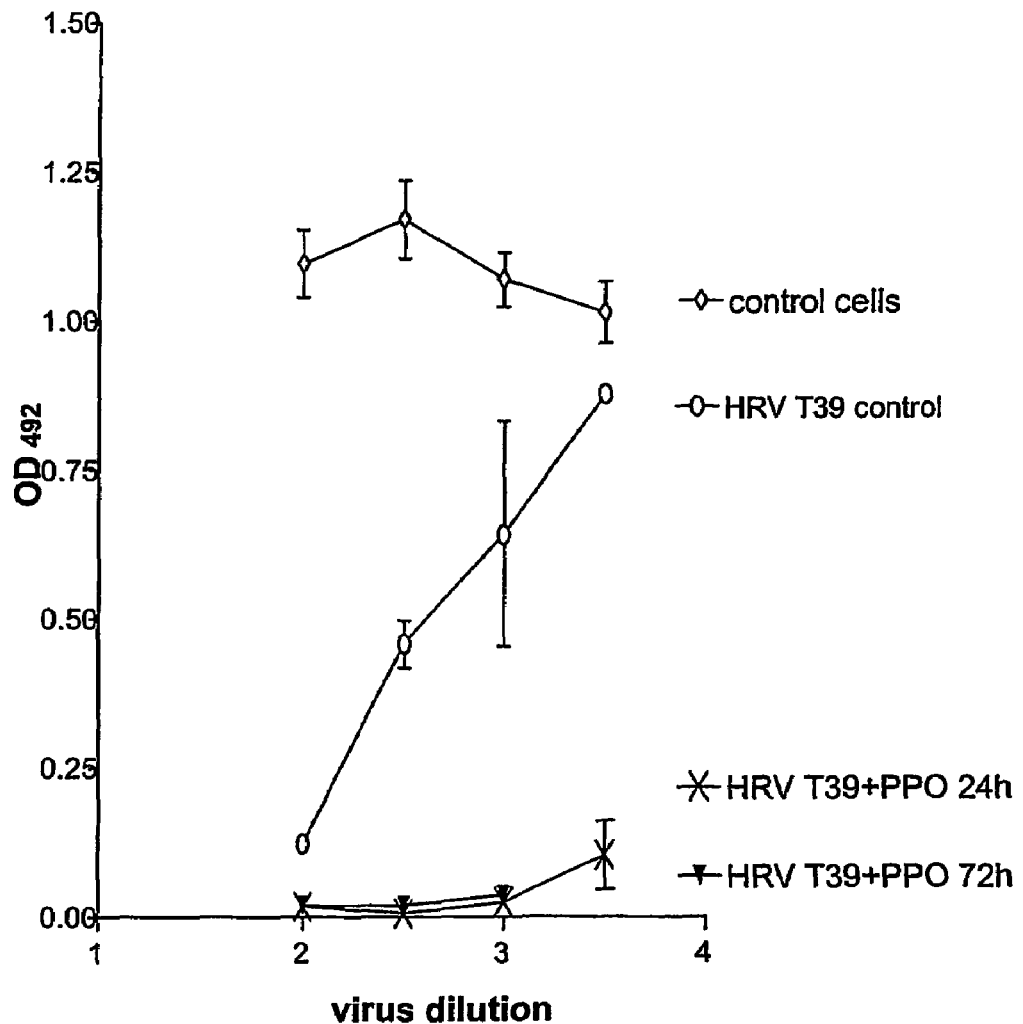
FIG. 3A illustrates that peppermint oil (designated PPO) potentiates the production of rhinovirus T39 (designated HRV T39).
Figure 3B:
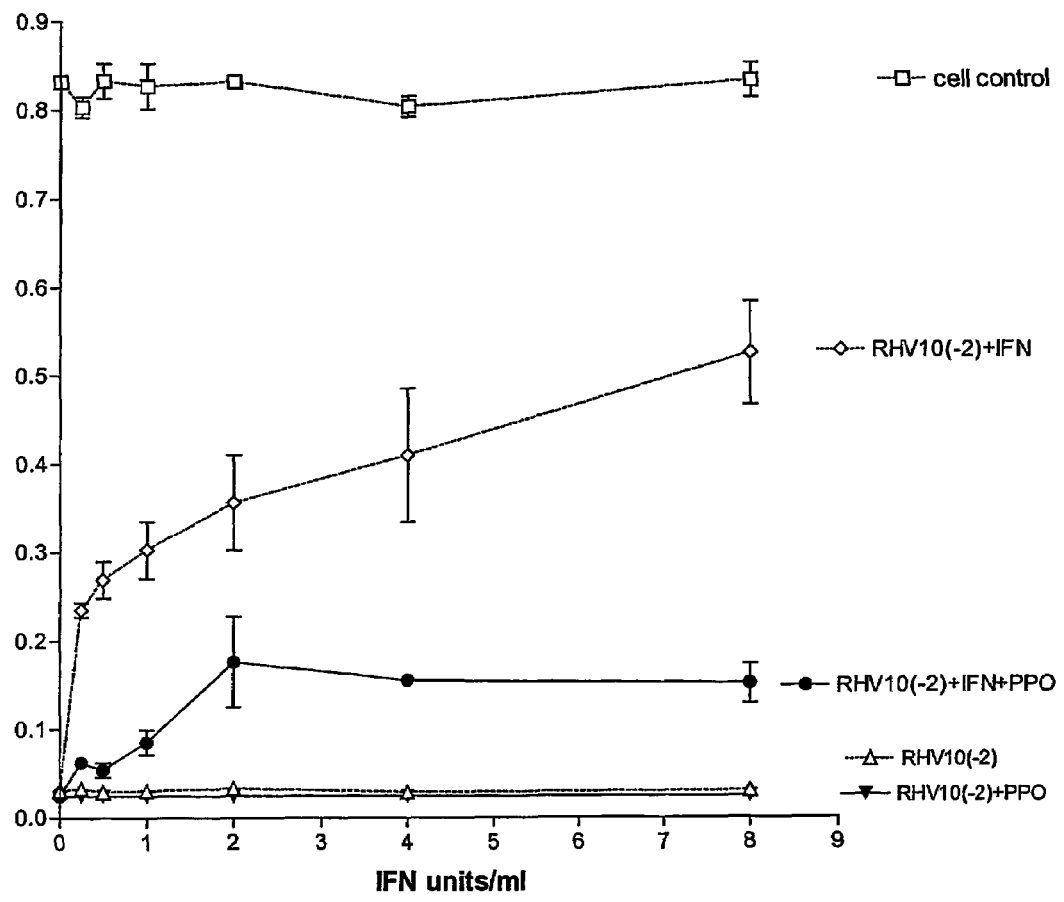
FIG. 3B illustrates that peppermint oil (designated PPO) downregulate the interferon-α system using rhinovirus 10 as challenge virus at a dilution of $10^{-2}$ (designated RHV10(-2) ). Interferon-α is designated IFN.
Figure 3C:
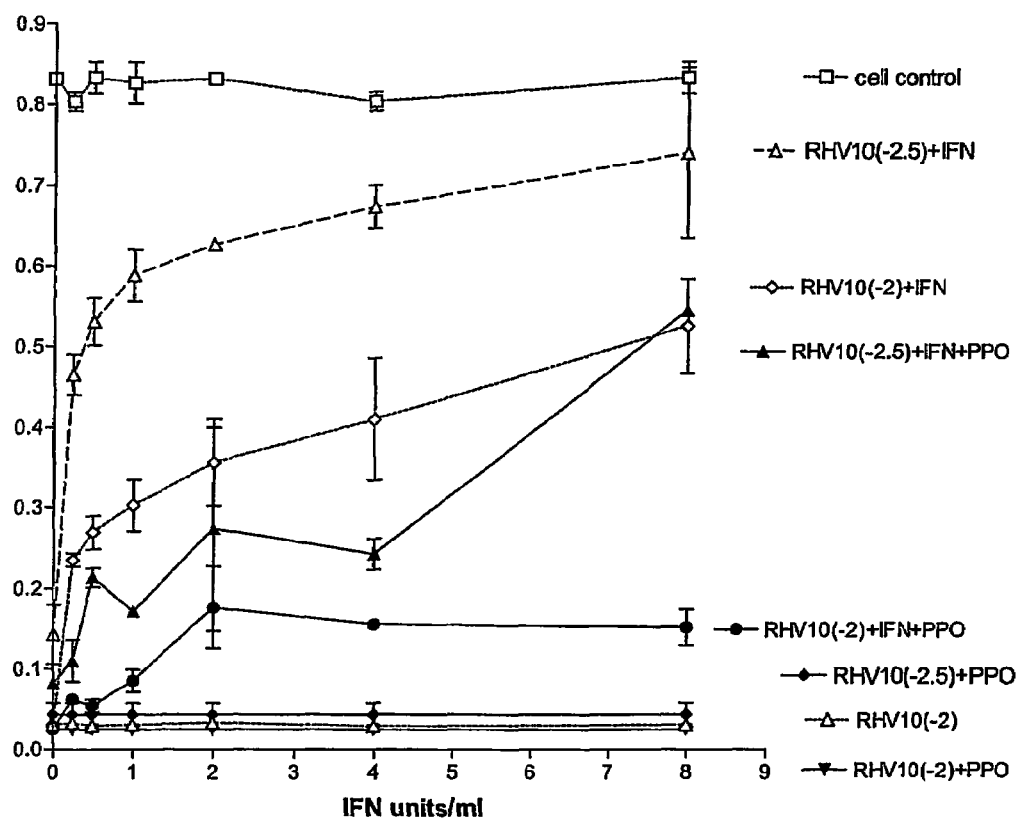
FIG. 3C illustrates that peppermint oil (designated PPO) downregulate the interferon-α (desingated IFN) system using rhinovirus 10 (designated RHV 10) as challenge virus at dilutions of $10^{-2}$ and $10^{-2.5}$.

FIGS. 3A, 3B, and 3C

To compare Japanese peppermint oil (PPO) with menthol a series of analog experiments as described in the preceding paragraphs were executed: monolayers of WISH cells in microtrays were titrated with rhinoviruses in the presence or absence of PPO at various dilutions in PBS (phosphate bufferede saline) of standard stock solutions of Japanese Peppermint Oil in 95% alcohol (supplied from the Rigshospitalets Pharmacy, Denmark) without any success as it turned out that PPO (diluted 1:100 in PBS) is rather toxic to WISH cells. Furthermore, dose-response curves between virus dilutions and dilutions of PPO in PBS proved without any meaning as no systematic decrease or dependency could be observed. The problem was solved when no pre-diluted PPO was added directly into the cell cultures infected with rhinoviruses. Instead, reproducible and meaningful results were obtained when the cultures were incubated with an extra microtray containing specific dilution of PPO in water (both trays were wrapped together in plastic foil and incubated in a small box with 5% $CO_2$/water at 33° C.). Apparently, the specific partial pressure of the PPO from the PPO-solution produced a certain amount of "PPO-gas", which in turn was absorbed by the relevant cell cultures infected with rhinovirus cultures, without causing toxic problems, per se in control cell cultures. Thus, microtrays filled with 200 µl of with standard PPO diluted 1:1000 in water incubated together with the microtray with cells and viruses proved to be very efficient when a non-toxic PPO-enviroment was to be established in the cell cultures infected with virus. The PPO treated wells had reproducibly a low, but distint odour of PPO after this treatment.

The results from such an experiment are shown in FIG. 3A: Two identical microtrays containing exactly the same virus dilutions in the appropriate wells are processed identically; one tray is incubated in an closed box containing no PPO but 5% CO2 at 33° C.; the other microtray is incubated together with a microtray filled with 200 µl PPO diluted 1:1000 in each well; both microtrays were wrapped together with plastic film and incubated in a closed box at the same conditions as the former box until a distinct CPE has developed in the control cell cultures (after 3-4 days) and processed using the MTT/MTS-PMS technigue as described previously (Berg et al., 1990; Berg et al., 2001; Berg et al., 2003) and below.

As expected the standard rhinovirus curve (HRV control) rises as a steep curve together with the increase in the dilution of the virus indicating that the virus infection depends on the innocculum, per se. At $10^{3.5}$ dilution it looks as no infection occurs, However, the parallel virus titration curve, in the presence of PPO 1:1000 (in the "empty" microtrays) proves to have a very dramatic influence on the production of virus, per se, as full production of virus now occurs irrespective of the dilution of the added virus; thus, the minute amount of PPO—received in a gaseous form by the wells containing the infected cells—is, indeed able to potentiate the production, remarkably. This phenomenons has not previously been described in the literature as far as PPO and Rhinovirus is concerned.

To elucidate if PPO should any influence on the interferon system, per se, a standard interferon titration was performed with rhinovirus and WISH cells (Berg et al., 2001) in the presence or absence of PPO-cf. above described experiment, as seen in FIG. 3B and 3 C; the results demonstrate directly that PPO also depresses the IFN-system, per se, especially at lower concentration range (i.e.: <10 units/ml) depending on the challenge virus concentration employed (cf. $10^{-2}$ vs. $10^{-2.5}$).

Similar results were observed using different vira (HRV 1A or HRV 14). It is therefore likely that other RNA viruses, in particular RNA viruses belonging to the respiratory viruses will react similarly to exposure to PPO.

Conclusions: Japanese Peppermint oil (PPO) increases the growth of rhinovirus 39 and other rhinoviruses and down-regulates the protective action of the natural, human leukocyte interferon system.

Example 4

FIGS. 4A, B,C,D,

Treatment of Common Cold Patients

In order to evaluate the new and surprising, in vitro, findings several studies were performed in common cold patients infected naturally. These studies had the objective to examine if the marked difference from the in vitro studies between PPO and Menthol also would be reflected in, in vivo, studies. The studies were undertaken essentially as described in patent application WO 02/09699, which is hereby incorporated by reference in its entirety.

The patients were treated with either menthol lozenges or PPO lozenges.

Menthol Lozenges
50 mg Troxerutin
25 mg Zn Gluconate
4-5 mg (−) menthol
882 mg sorbitol
10 mg magnesium stearat PPO Lozenges
50 mg Veneruton©
25 mg Zn Gluconate
4-5 mg (−) menthol882 mg sorbitol
10 mg magnesium stearat In order to evaluate the effect of treatment the following Patients Diary was filled in by the patients and symptom score was calculated.

Patients Diary

This scheme should preferably be filled out in the evening. How are your current condition with regard to the symptoms below. In the scheme below, please state the strength of your symptoms today by inserting an X at the appropriate place: every symptom should have points: 0 means that you have not had any symptoms at all; 4 means that you have had the worst symptoms available; etc. 0=no symptoms, 1=a minimum of symptoms; 2=unpleasant symptoms; 3=considerably unpleasant symptoms; 4 =very unpleasant symptoms

|  | Symptom points | | | | |
| --- | --- | --- | --- | --- | --- |
|  | 0 | 1 | 2 | 3 | 4 |
| Cough | | | | | |
| Headache | | | | | |
| Hoarseness | | | | | |
| Nasal discharge | | | | | |
| Sneezing | | | | | |
| Nasal obstruction | | | | | |
| Sore throat | | | | | |
| Irritated throat | | | | | |
| Malaise | | | | | |
| Sore muscles | | | | | |
| Fever | | | | | |

Have you had any side effects of the treatment? Yes ☐ No ☐
Specify_____

Do you also take other medical treatment or other kinds of treatment apart from this test treatment? Yes ☐ No ☐
Specify_____

The scheme above may preferable be used for identifying persons in need of a treatment according to the invention and to compare the effect with other treatments or placebo.

A total score of 3 to 5 or less is-regarded to be a normal condition.

Most of the patients included in this section have been treated at Doctor's Office within 24-30 h after the onset of the classical common cold symptoms; preferentially, patients with fewer are allergic rhinitis or the like were excluded from these studies. Each patient was instructed to fill out the patients diary every day (day 0=1$^{st}$ visit to the Doctor's Office) and to follow the mode of administration: one lozenge should be applied on or under the patient's tongue and it should melt in a minimum period of 4-5 min. (no fluid or food should be taken the next 15-20 min.) If necessary, the patient could take the next lozenge after 30 min.; a total number of 57 lozenges per day was equal to the maximal dose per day. Last lozenge should be taken just before bedtime. Treatment was in general continued for 3 to 4 days.

A few patients—who are not included in the enclosed figures as they reported back by telephone—expressed a surprisingly fast recovery after treatment with menthol-lozenges, as already less than 5-6 of the menthol-lozenges stopped the rhinoea and sore throat—this effect was not observed with similar patients treated with the PPO-lozenges.

To further examine quantitatively the efficacy of the treatment with Menthol-lozenges common cold patients who all had reported to the Doctor's Office within 24-30 h subsequent to the appearance of the typical symptoms (no fewer, beginning rhinoea, sneezing, etc.) were treated for 3-4 days with Menthol lozenges as described above.

Figure 4A:
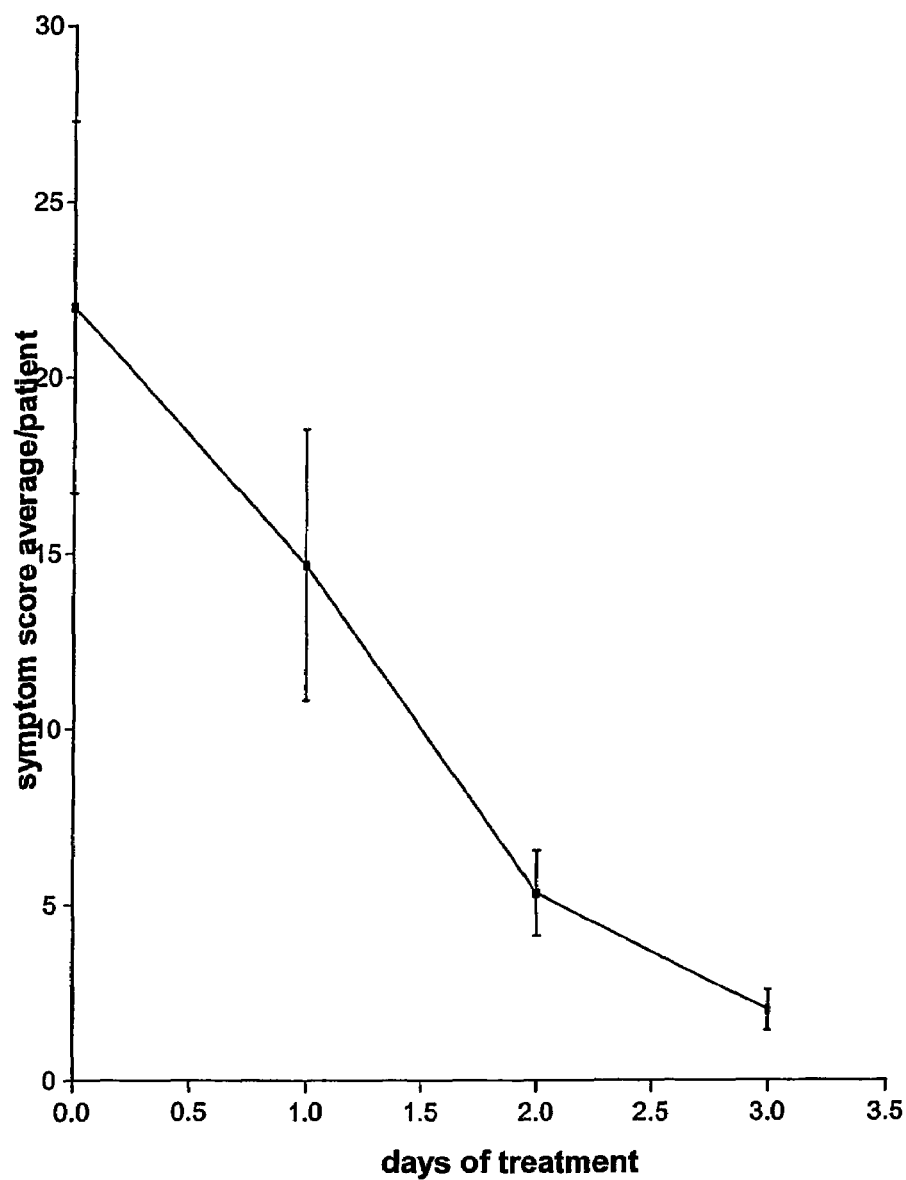
FIG. 4A illustrates the total mean symptom score per common cold patient treated with menthol-lozenges. The curves show the average and standard deviation from 3 patients (patients no. 161202, 020403 and 270403), wherein treatment was initiated 24 h p.i.

The patients returned their diaries and the specific symptoms scores (SS) were evaluated as shown in FIG. 4A. The following results were noted:

FIG. 4A shows the symptoms score of 3 patients treated with menthol lozenges, where treatment was initiated 24 h post infection (p.i.)

Table 1. Reduction in symptom score (SS) using menthol-lozenges (cf. FIG. 4A)
reduction in SS after 1 day treatment=32%
reduction in SS after 2 days treatment=77%
reduction in SS after 3 days treatment=90%

These results are more favorable compared to an earlier study with a group of similar patients treated with the PPO-lozengers using a similar adminstation regime (see table 2 and FIG. 4E). This study is described in detail in previous patent appl. No. WO 02/09699, example 7. 8 patients were treated with PPO-lozenges without $Zn^{2+}$. 12 patients were treated with PPO-lozenges. Treatment was initiated 24-36 h p.i.

Figure 4B:
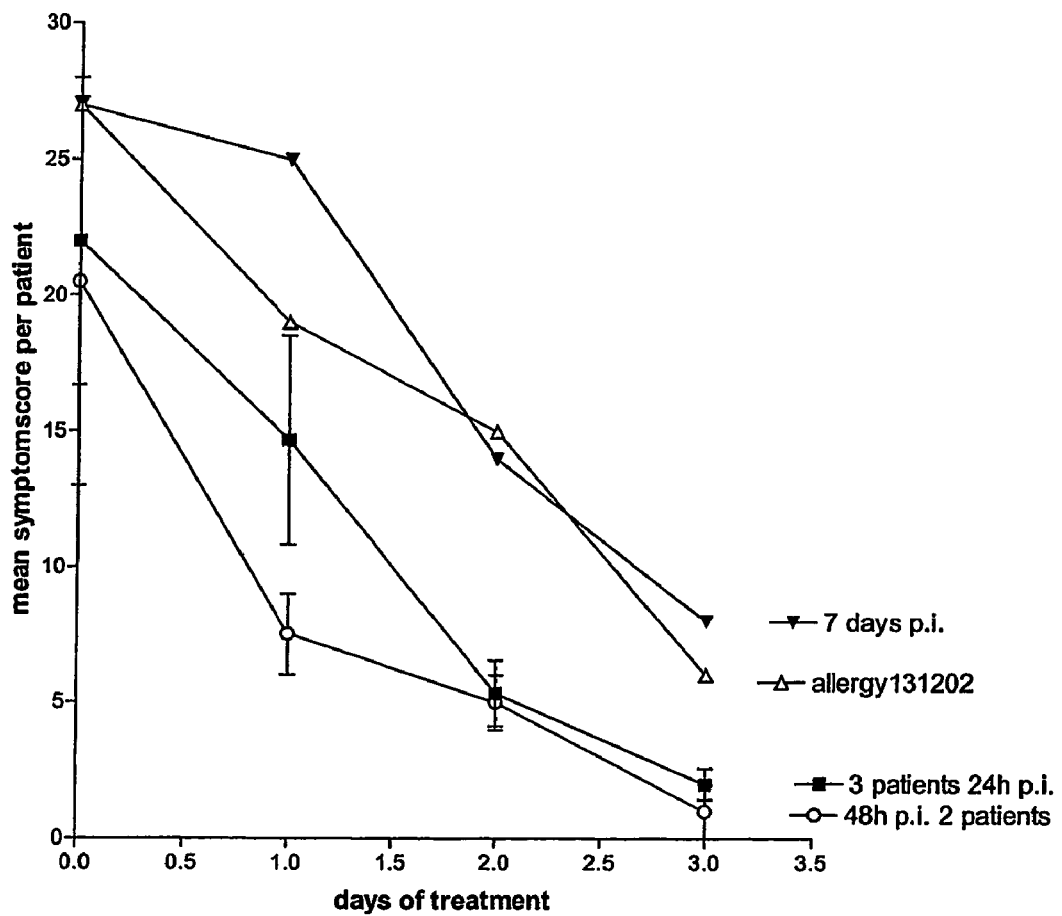
FIG. 4B illustrates the total mean symptom score per common cold patient treated with Menthol-lozenges. The curves shows the average and standard deviation from groups of patients grouped according to when treatment was initiated (24 h, 48 h and 7 days p.i.).

The symptom score of the above-mentioned group of 3 patients (treatment initiated 24h p.i. ) is also displayed in FIG. 4B, together with a group of 2 patients, (treatment initiated 48h p.i). As can be seen both groups have a similar 90% reduction in SS at day 3. Allergy and treatment initiated 7 days p.i. change dramatically the outcome, and are therefore routinely excluded in the usual protocol.

Figure 4C:
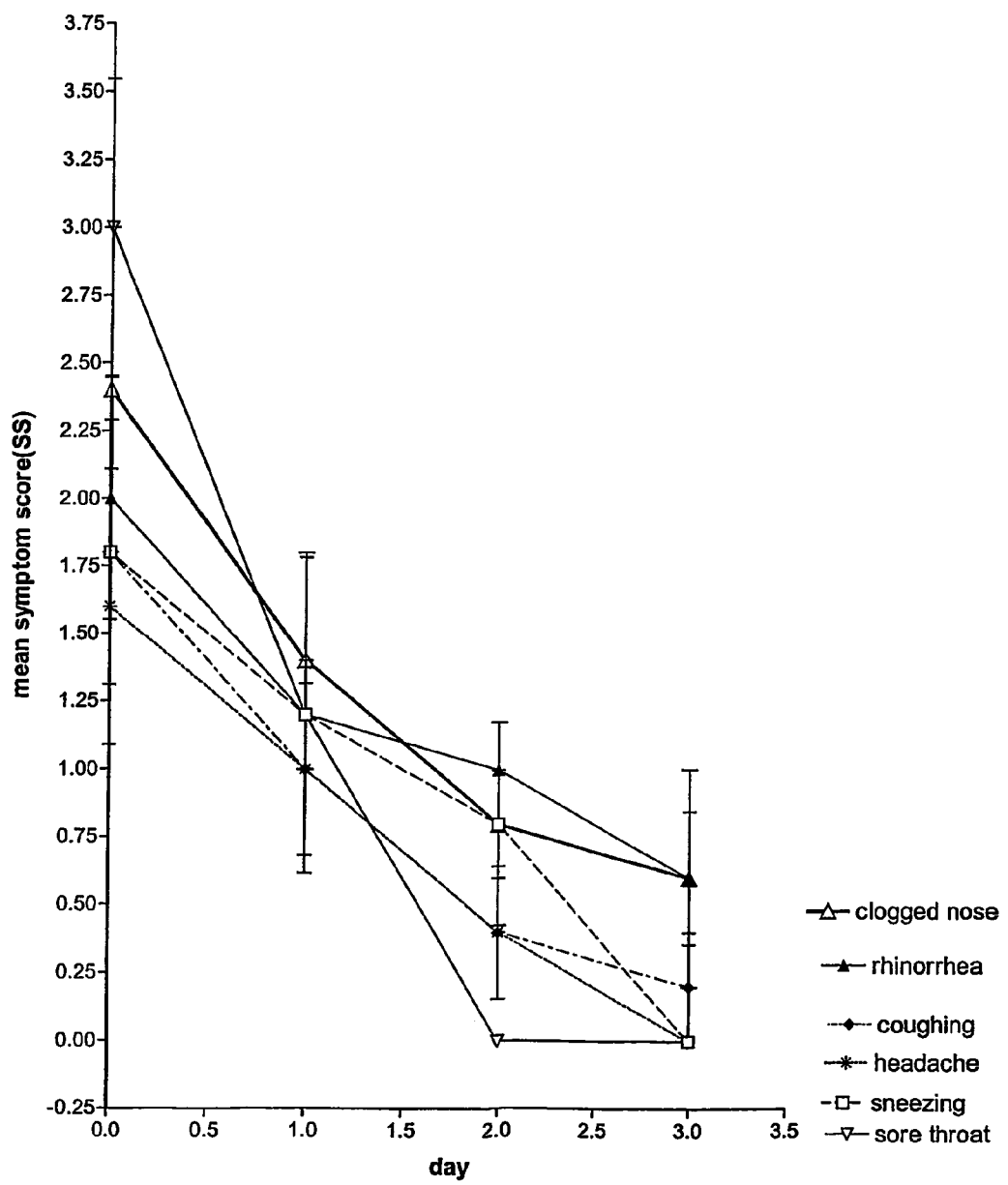
FIG. 4C illustrates differential symptom score from 5 common cold patients treated with Menthol-lozenges. The curves show symptom score for rhinitis/rhinorrhea, sore throat, sneezing, clogged nose, coughing and headache.
Figure 4D:
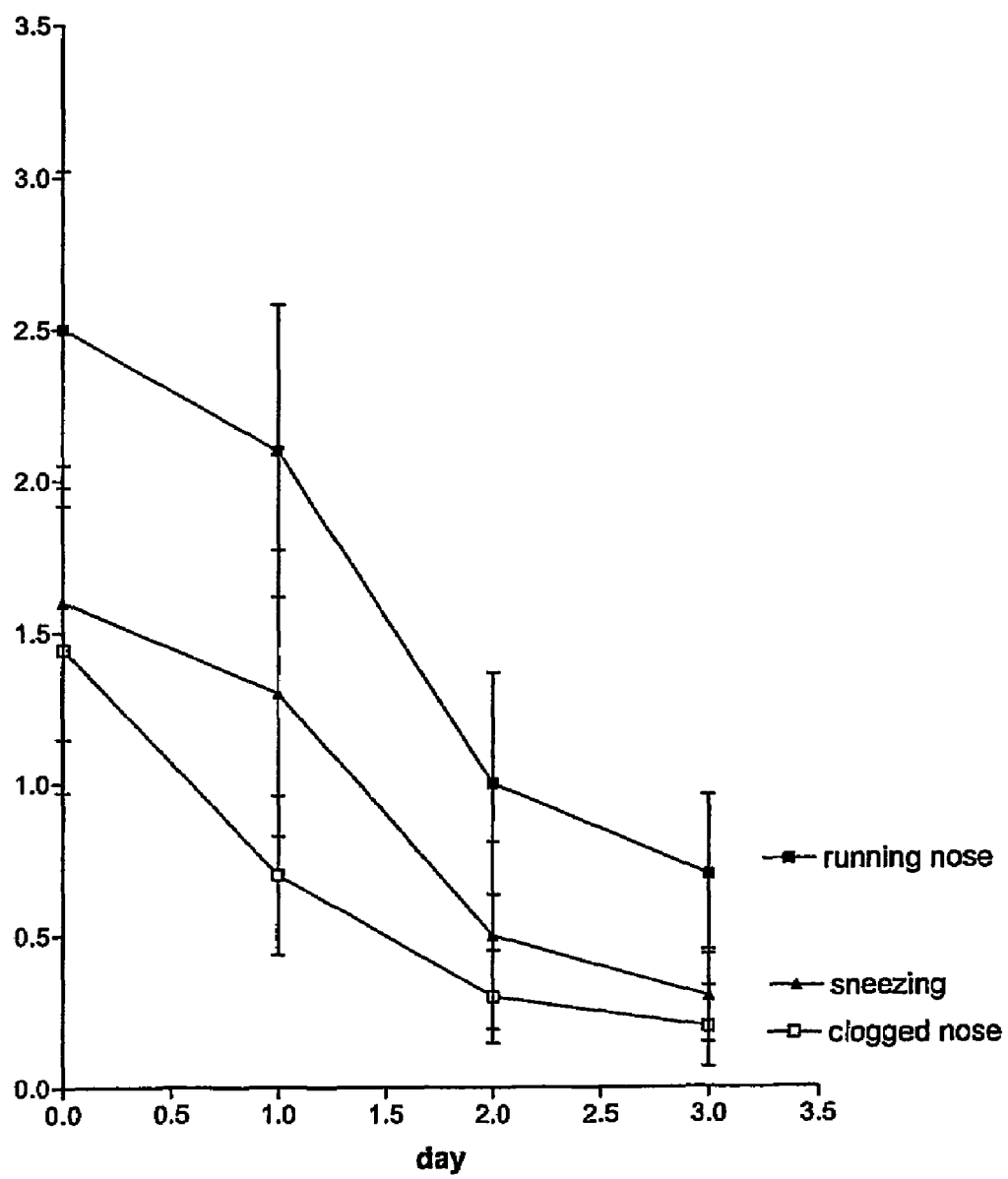
FIG. 4D illustrate differential symptom score from 10 patient treated with PPO-lozenges (treatment initiated 24-36 h p.i.). The curves show symptom score for running nose, sneezing and clogged nose.
Figure 4:
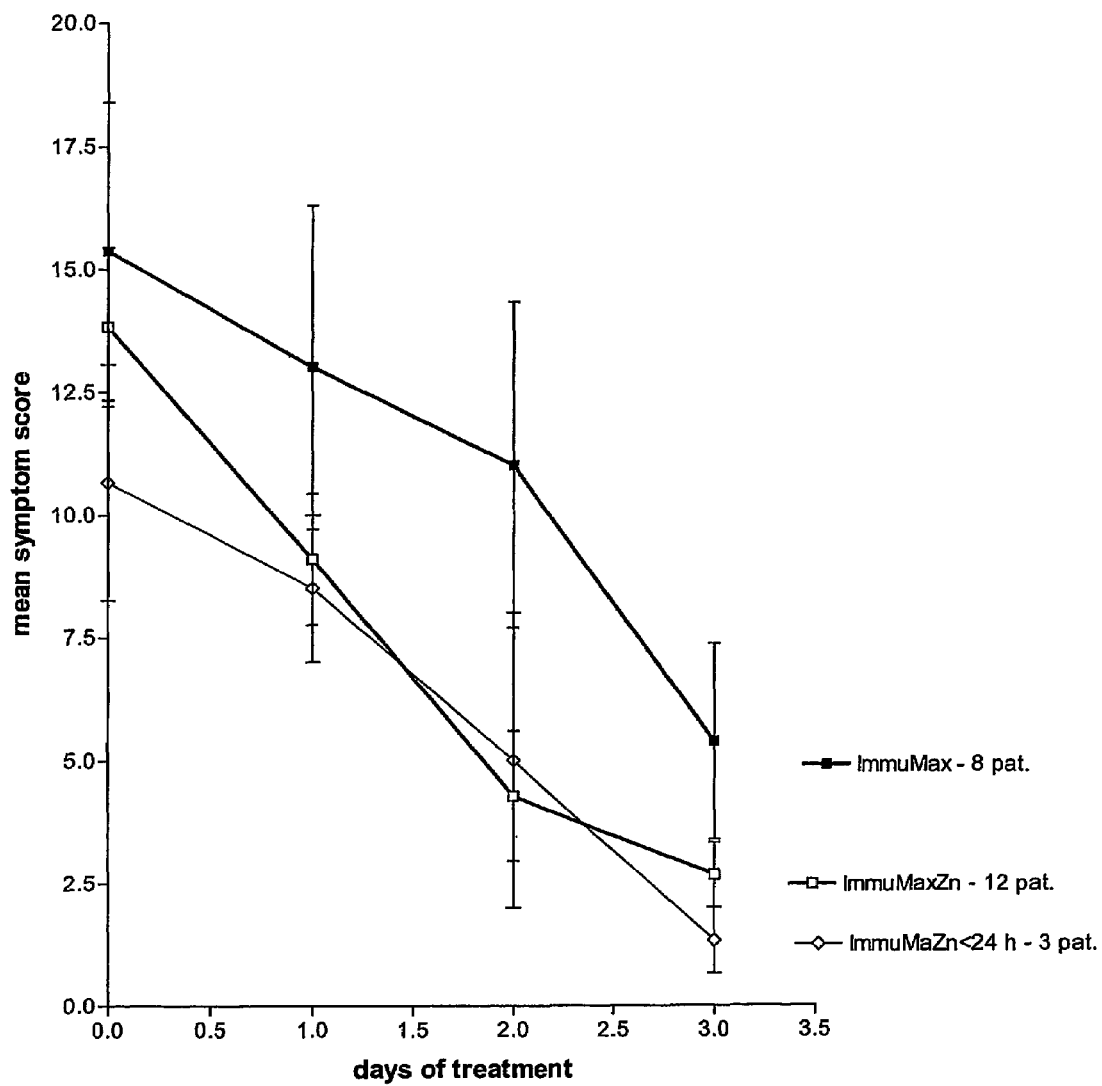
FIG. 4E illustrates total mean symptom score for naturally infected common cold patients treated with PPO-lozenges with (ImmuMaxZn) or withour $Zn^{2+}$ (ImmuMax). Treatment was initiated within 24-36 h subsequent to clinical diagnosis.
FIG. 4F illustrates total mean symptom score for naturally infected common cold patients treated with PPO-lozenges with (ImmuMaxZn) or withour $Zn^{2+}$ (ImmuMax). Treatment was initiated within 24 h subsequent to clinical diagnosis.
Figure 4:
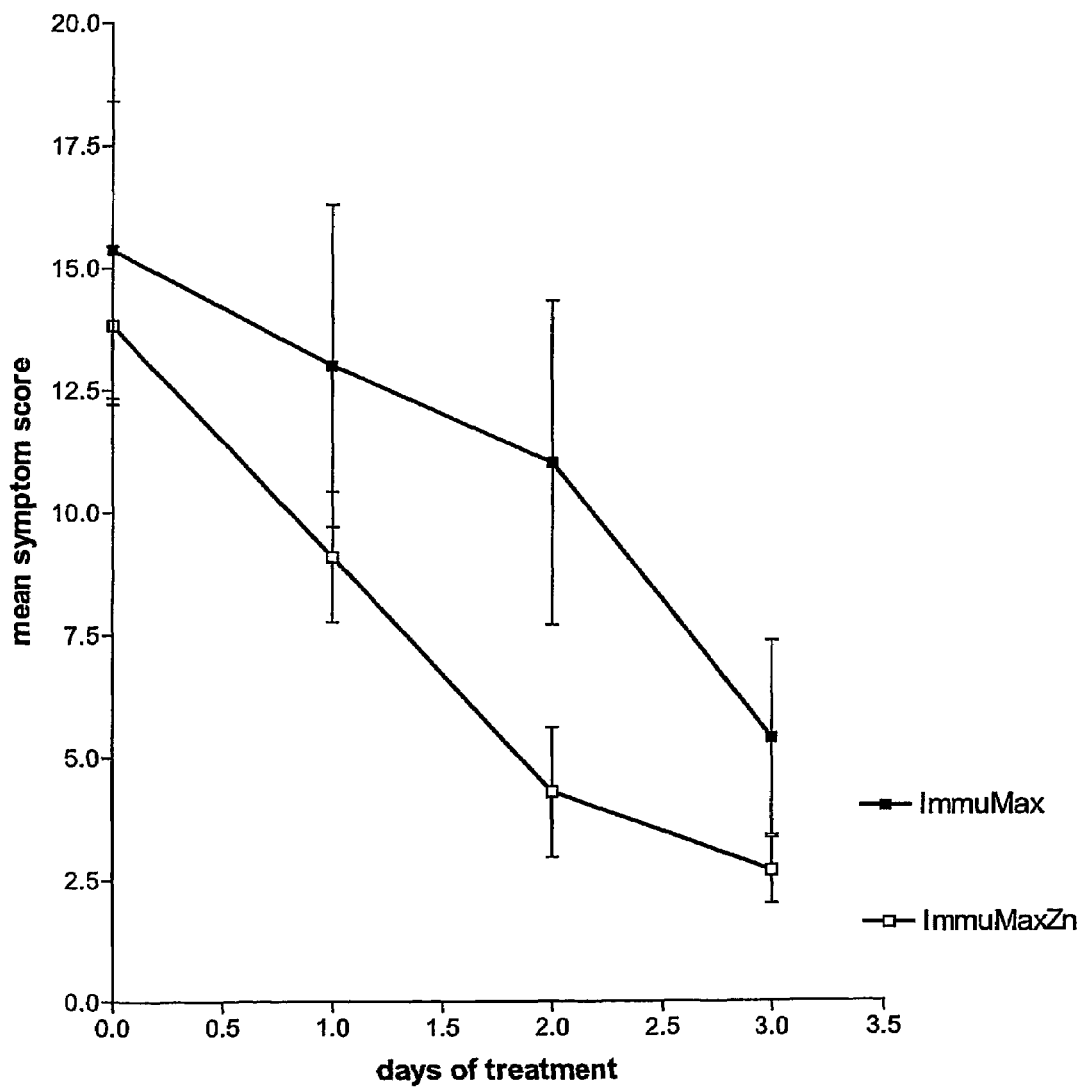

The two groups of patients in FIG. 4B were further examined in a group of 5 (shown in FIG. 4C) with regards to differential symptom scores: it appears that 3 symptoms are 100% eliminated at day 3 after treatment with menthol-lozenges. This was not observed with a parallel treatment using PPO-lozenges, cf. FIG. 4D, where some symptoms remains after 3 days treatment.

Table 2. Reduction in symptom score (SS) using PepperMint Oil (PPO)-lozenges (cf. FIG. 4E)
reduction in SS after 1 day treatment=34% reduction in SS after 2 days treatment=71% reduction in SS after 3 days treatment=80%

Furthermore, the variation in SS between the two groups treated with menthol- or PPO-lozenges, respectively (compare results of FIGS. 4D and 4E) were significantly smaller in the menthol-treated group as a more constant and fast response was noted; An additional advantage of the menthol-lozenges is that the metal taste from the ZnGluconate was practically eliminated in the menthol lozenges.

Conclusion: The In vitro findings indicate that Menthol has specific antiviral effects vs. rhinoviruses (-1A, -14, and -T39). These findings may explain the reason for ImmuTroxZn-Menthol lozenges appear to be more efficient compared to ImmuTroxZn-PPO lozenges in the treatment of common cold.

Example 5

One patient who experienced the usual common cold symptoms (incl. a minor fever) was treated with a special lozenge containing no Zinc, a 3× higher content of Troxerutin than the Menthol-lozenge of example 4 (150 mg per lozenge) and 5 mg Menthol (ImmuTrox(150 mg)Menthol(5 mg)). The administration was performed as described in example 4.

After the first two lozenges the sore throat disappeared within 30 min.; coughing and rhinitis decreased substantially within 2-3 h; a total of 4 lozenges were applied the first day with and the treatment continued the following two days (4 lozenges per day): more than 80-90% of the usual symptoms were absent at day 3.

Conclusion: Lozenges comprising only Troxerutin and Menthol are also efficient in the treatment of common cold.

Example 6

Male patient (MT) allergic to certain grass species (*Alopecurus pratensis*, etc.) presented also a common cold at the Doctor's Office 3-4 days after the allergy and the cold had started; the patient was unhappy about all the rhinoea and was coughing. The patient was treated with ImmuTroxZnMent lozenges (50 mg Troxerutin, 25 mg Zn Gluconate, and 5 mg Menthol) as described in example 4 and returned the protocol 3-4 days later; on the day of initiation of treatment the SS was 25; 24 h later the SS was reduced to 7, 48 h later SS was reduced to 1; 72 h later: SS=0. The patient noted that his allergy was significantly reduced. Several weeks later the patient reported that his grass allergy had changed and that it was no longer so bothersome.

Conclusion: it appears that the ImmuTroxZnMen lozenges also has a direct anti-allergic effects. This observation later has been reported by other patients suffering from allergic rhinitis and the like.

REFERENCES

Berg, K, Andersen, H. and Owen, T. C. (2003) The regulation of rhinovirus infection in vitro by IL-8, HuIFN-alpha, and TNF-alpha. APMIS (submitted).

Berg, K., Bolt, G., Andersen, H. and Owen, T. C. (2001) Zinc potentiates the antiviral action of human interferon-alpha tenfold. J.Ifn.Cytokin.Res. 21, 471-474.

Berg, K. and Owen, T. C. (2003) The usage of the MTS/PMS-method as a tool for measurements of rhinovirus infections invitro and its application for quantification if antiviral activity. APMIS submitted.

Hansen, M. B., Nielsen, S. E. and Berg, K. (1989) Re-examination and further development of a precise and rapid dye method for measuring cell growth/cell kill. J.Immunol.Methods 119, 203-210.

Arruda, E., et al., Location of human rhinovirus replication in the upper respiratory tract by in situ hybridization. J.Inf..Dis.—JID, 1995. 171(May): p. 1329-1333.

Berg, K., Simonsen, B. H., Hansen, M. B., and Nielsen, S., 1989, A Method for Analysing a sample for the presence of a biological substance, especially a virus, use of the method for quantitative determination of biological substances and agents for use in as we as novel substances detected by the method, PCT/DK/, 89/00010, pp. 1.

Berg, K., Hansen, M. B., and Nielsen, S. E., 1990, A sensitive bioassay for presice quantification of interferon activity as measured-via the mitichondrial dehydrogenase function in cells (MTT-method), AMPIS, 98, 156.

Berg, K., and Owen, T. C., 2001a, The usage of the MTS/PMS-method as a tool for measurements of rhinovirus infections in vitro and its application for quantification of antiviral activity, J. APMIS, (submitted).

Broide, D. H. et al.: J. Allergy Clin.Immunol. 89:958 (1992).

Cate, T., R. B. Couch, and K. M. Johnson, Studies with rhinoviruses in volunteers: production of illness, effects of naturally acquired antibody and demonstration of a protective effect not associated with serum antibody. J.Clin.Invest., 1964. 43(no. 1): p. 56-67.

Cate, T. R., G. Douglas, and R. B. Couch, Interferon and resistance to upper respiratory virus illness. Proc.Soc.Exp.Biol.Med., 1969. 131: p. 631-636.

Farr, B., et al., A method for measuring polymorphonuclear leukocyte concentration in nasal mucus. Acta Otolaryngol (Stockh), 1984. suppl. 413: p. 15-18.

Fachet, F. and M. Gabor, Effect of flavonoids on delayed-type hypersensitivity in inbred mice. Flavonoids., ed. F.e. al. 1977. 395-399.

W. Felix, The actions of hydroxyethylrutoside on edema formation due to various capillary damaging substances. Flavonoids and Bioflavonoids, ed. F.e. al. 1977: Elvier. 411-416.

Gabor, M. and G. Blazso, Effect of o-beta-hydroxyethyl-rutin on rat-paw eodema induced by carrageenin and prostaglandin El. Flavonoids., ed. F.e. al. 1977: Elsvier. 38186.

Gaffey, M. and e. al, Ipratropium bromide treatment of experimental rhinovirus infection. Antimicrob.Agents Chemother., 1988. 32: p. 1644-1647.

Gern, J. E., et al., Rhinovirus enters but does not replicate inside monocytes and airway macrophages. J.Immunol., 1996.: p. 621-627.

Gern, J. E. and W. W. Busse, Association of rhinovirus infections with asthma. Clinical Microbiology Reviews, 1999. 12 (no. 1, January): p. 9-18.

Ginsburg, I., Could synergistic interactions among reactive oxygen species, proteinases, membrane-perforating enzymes, hydrolases, microbial hemolysins and cytokines be the main cause of tissue damage in infectious and inflammatory conditions? Med. Hypotheses, 1998. 51(4): p. 337-46

Graham, N., et al., Adverse effects of aspirin, acetaminophen and ibuprophen on immune function, viral shedding and clinical status in rhinovirus-infected volunteers. J.Infect..Dis., 1990. 162: p. 1277-1282.

Grünberg, K. and P. J. Sterk, Rhinovirus infections: induction and modulation of airways inflammation in asthma. Clinical and Experimental Allergy, 1999. 29(suppl. 2): p. 65-73.

Gwaltney, J. Mj., Rhinovirus infection of the normal human airway. Review american journal of respiratoty and critical care medicine, 1995. 152(4): p. S36-S39.

Hansen, M. B., Nielsen, S. E., and Berg, K., 1989, Re-examination and further development of a precise and rapid dye method for measuring cell growth/cell kill, J.Immunol. Methods, 119, 203.

Hayden, F. G., et al., Human nasal mucosal responses to topically applied recombinant leukocyte A interferon. The journal of infectious diseases, 1987. 156(1): p. 64-72.

Hayden, f., J. J. Gwaltney, and R. Colonno, Modification of experimental rhinovirus colds by receptor blockade. Antiviral Res., 1988. 9: p. 233-247.

Hider, R., Liu, Z D. and Khodr, H H, 2001, Metal chelation of polyphenols, Methods in Enzymology, vol 335, 190-203.

Ihrcke, N. S., et al., Role of heparan sulfate in immune system-blood vessel interactions. Review. Immunology today, 1993. 14(10): p. 500-505.

Jackson et al., Arch. Internal. Med. 101:267-278, 1958

Johnston, S. L., et al., Use of polymerase chain reaction for diagnosis of picornavirus infection in subjects with and without respiratory symptoms. Journal of clinical microbiology., January 1993.: p. 111-117.

Monto, A. and e. al, Ineffectiveness of postexposure prophylaxis of rhinovirus infection with lowdose intranasal alpha 2b interferon in families. Antimicrobiol. Agents Chemother., 1989. 33: p. 387-390.

Mussad S B, Macknin M L, Medendorp S V nad Mason P, 1996, Zinc gluconate lozenges for tresting the common cold, a randomised, double blind, placebo-controlled study.

Naclerio, R. and e. al, Kinins are generated during experimental rhinovirus colds. J,Infect.Dis., 1988. I57: p. 133-142.

Proud, D. and e. al, Kinins are generated in nasal secretions during natural rhinovirus colds. J.Infect.Dis., 1990. 161: p. 120-123.

Rotbart, H. A., *Antiviral therapy for interoviruses and rhinoviruses*. Antiviral Chemistry & Chemotherapy, 2000. 11: p. 261-271.

Shimoi K, Noriko S, Nozawa R, Sato M, Amano I, Nakayama T and Kinae N. 2001, Deglucuronidation of a flavonoid, luteolin monoglucuronide during inflammation. Drug metabolism and disposition, vol. 29, p. 1521-1524.

Spector, S. L., The common cold: current therapy and natural history. J.allergy. clin immunol., 1995. 95(5 part 2): p. 1133-1138.

Sperber, S. P., P. Levine, and e. al, Ineffectivness of recombinant interferon-beta serine nasal drops for prophylaxis of natural colds. J.Infect.Dis., 1989.160: p. 700-705.

Turner, R. B., et al., Sites of virus recovery and antigen detection in epithelial. cells during experimental rhinovirus infection. Acta Otolaryngol (Stockh), 1984. suppl. 413: p. 9-14.

Van Damme, J., et al., A novel. NH2-terminal sequence-characterized human monokine possessing neutrophil chemotactic, skin-reactive, and granulocytosis-promoting activity. J.exp.med., 1988. 4: p.1364-1376.

Winther, B., et al., Study of bacteria in the nasal cavity and nasopharynx during naturally acquired common colds. Acta otolaryng., 1984. 98: p. 315-320.

Winther, B., et al., Light and scanning electron microscopy of nasal biopsy material from patients with naturel acquired common colds. Acta otolaryng., 1984. 97: p. 309-318.

Winther, B., et al., Histopathological examination and enumeration of polymorphonuclea leukocytes in the nasal mucosa during experimental rhinovirus colds. Acta otolaryng.supp., 1984. 413: p. 19-24.

Winther, B., et al., Intranasal spread of rhinovirus during point-inoculation of the nasal mucosa. Jpn. JAMA, 1987. 5: p. 99-103.

Winther, B., et al., Lymphocyte subsets in normal airway of the human nose. Arch.otosryng.head neck surg., 1987.113: p. 59-62.

Winther, B., Effects on the nasal mucosa of upper resiratory viruses (common cold), 1993, University of Copenhagen.

Winther, B., Effects on the nasal mucosa of upper respiratory viruses (common cold). Laegeforeningens Forlag, 1993

Winther, B., et al., Viral-induced rhinitis. Am.J.Rhinology, 1998. 12(no. 1,January-February): p. 17-20.

The invention claimed is:

1. A pharmaceutical composition comprising
one or more purified flavonoids; and
purified menthol, in a state of purity such that the purified menthol has a direct antiviral effect in vitro on rhinovirus in WISH cells, or potentiates the antiviral effect in vitro of human interferon -$\alpha$-2b (Intron A) on rhinovirus in WISH cells.

2. The pharmaceutical composition according to claim 1, wherein said composition also comprises a pharmaceutically acceptable metal complex and/or metal salt.

3. The pharmaceutical composition according to claim 2, wherein said metal is zinc.

4. The pharmaceutical composition according to claim 2, wherein the metal is zinc selected from the group consisting of $Zn^{2+}$ aminochelates , $Zn^{2+}$ amino acid chelates, Zn(acetate)$_2$, $Zn^{2+}$ DL-methionine, $Zn^{2+}$ L-methionine, ZnGluconate and PolaPreZinc®.

5. The pharmaceutical composition according to claim 1, wherein said composition is useful for oral and/or nasal administration.

6. The pharmaceutical composition according to claim 1, wherein said composition is selected from the group consisting of lozenges, troches, capsules, syrups, tablets, lollipops, solutions, dispersions, suspensions, powders, microperes, chewing tablets, chewing gums, sprays, droppers, pipettes and pills.

7. The pharmaceutical composition according to claim 1, wherein said composition is a slow-release composition.

8. The pharmaceutical composition according to claim 1, wherein said composition is lozenges.

9. The pharmaceutical composition according to claim 1, wherein said composition is essentially free of crude plant extracts.

10. The pharmaceutical composition according to claim 1, wherein said composition is essentially free of other terpenes than menthol.

11. The pharmaceutical composition according to claim 1, wherein said composition is essentially free of one or more compounds selected from the group consisting of menthone, menthyl acetate, limonene and neomenthol.

12. The pharmaceutical composition according to claim 1, wherein one or more flavonoids are chelating a metal.

13. The pharmaceutical composition according to claim 1, wherein the metal is $Zn^{2+}$.

14. The pharmaceutical composition according to claim 1, wherein the flavonoid is selected from the group consisting of flavonoids of the general formula:

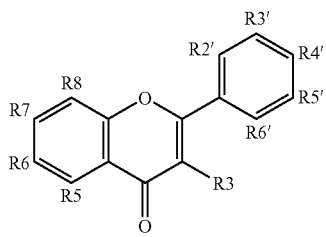

and the general formula:

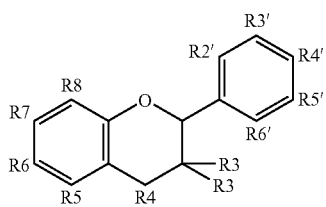

Wherein
R2' can be selected from: —H
  —OH
R3' can be selected from: —H
  —OH
  —OCH$_3$
  —OCH$_2$CH$_2$OH
R4' can be selected from: —H
  —OH
  —OCH$_3$
  —OCH$_2$CH$_2$OH
R5' can be selected from: —H
  —OH
  —OCH$_3$
  —OCH$_2$CH$_2$OH
R6' is —H;
R3 including R3$_1$ and R3$_2$ can individually be selected from: —H
  —OH
  —O-rutinose
  —O-glucoside
  —O-glucose-p-coumaric acid
  —SOH
  —O-rhamnose
R4 can be selected from: —(O)
  —OH
R5 can be selected from: —H
  —OH
  —O—CH$_2$CH$_2$OH
R6 can be selected from: —H
  —OH
  —OCH$_3$
R7 can be selected from: —H
  —OH
  —O-glucose
  —OCH$_3$
  —OCH$_2$CH$_2$OH
  —O-glucuronic acid
  —O-rutinose
  —O-rhamnoglucoside R8 can be selected from: —H
  —OH.

15. The pharmaceutical composition according to claim 1, wherein the flavonoid is selected from the group consisting of troxerutin, venoruton, hesperitin, naringenin, nobiletin, tangeritin, baicalein, galangin, genistein, quercetin, apigenin, kaempferol, fisetin, rutin, luteolin, chrysin, taxifolin, eriodyctol, catecithin, epicatechin gallate, epigallocatechin gallate, flavone, sideritoflavone, hypolaetin-8-O-Gl, oroxindin, 3-hydroxyflavone, morin, quercetagetin-7-O-Gl, tarnbuletin, gossypin, hipifolin, naringin, leucocyanidol, amentoflavone and derivatives thereof and mixtures thereof.

16. The pharmaceutical composition according to claim 1, wherein said flavonoid is not a naturally occurring flavonoid.

17. The pharmaceutical composition according to claim 1, wherein said flavonoid is a rutoside.

18. The pharmaceutical composition according to claim 1, wherein at least one flavonoid is a rutoside aglycone.

19. The pharmaceutical composition according to claim 1, wherein said flavonoid is a hydroxyethylrutoside.

20. The pharmaceutical composition according to claim 1, wherein at least one flavonoid is a hydroxyethythyrutoside aglycone.

21. The pharmaceutical composition according to claim 1, wherein said composition comprises a mixture of hydroxyethylrutosides.

22. The pharmaceutical composition according to claim 1, wherein said composition comprises a mixture of mono-, di-, tri- and tetrahydroxyethylrutosides.

23. The pharmaceutical composition according to claim 1, wherein at least one flavonoid is troxerutin.

24. The pharmaceutical composition according to claim 1, where at least one flavonoid is troxerutin aglycone.

25. The pharmaceutical composition according to claim 1, wherein the flavonoid is veneruton.

26. The pharmaceutical composition according to claim 1, wherein said purified menthol is at least 90% pure.

27. The pharmaceutical composition according to claim 1, wherein the composition is in a form suitable for nasal administration.

28. The pharmaceutical composition according to claim 27, wherein the composition is in a form suitable for aerosol administration.

29. The pharmaceutical composition according to claim 28, wherein the composition is provided in a pressurized pack which further comprises a propellant.

30. The pharmaceutical composition according to claim 1, wherein said purified menthol is at least 98% pure.

* * * * *

UNITED STATES PATENT AND TRADEMARK OFFICE
CERTIFICATE OF CORRECTION

PATENT NO. : 7,585,890 B2  Page 1 of 1
APPLICATION NO. : 10/532341
DATED : September 8, 2009
INVENTOR(S) : Kurt Frimann Berg It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 468 days.

Signed and Sealed this

Fourteenth Day of September, 2010

David J. Kappos
*Director of the United States Patent and Trademark Office*